United States Patent
Zipse et al.

(10) Patent No.: US 8,500,793 B2
(45) Date of Patent: Aug. 6, 2013

(54) HELICAL IMPLANT HAVING DIFFERENT ENDS

(75) Inventors: Achim Zipse, Baden-Baden (DE); Andreas Block, Lubeck (DE); Pauline Weise, Pforzheim (DE); Martin Schlun, Herxheim Bei Landau/Pfalz (DE)

(73) Assignee: C. R. Bard, Inc., Murray Hill, NJ (US)

( * ) Notice: Subject to any disclaimer, the term of this patent is extended or adjusted under 35 U.S.C. 154(b) by 952 days.

(21) Appl. No.: 12/440,415

(22) PCT Filed: Sep. 7, 2007

(86) PCT No.: PCT/EP2007/059407
§ 371 (c)(1),
(2), (4) Date: Mar. 6, 2009

(87) PCT Pub. No.: WO2008/028964
PCT Pub. Date: Mar. 13, 2008

(65) Prior Publication Data
US 2010/0004725 A1    Jan. 7, 2010

Related U.S. Application Data

(60) Provisional application No. 60/842,853, filed on Sep. 7, 2006.

(51) Int. Cl.
*A61F 2/06* (2013.01)
(52) U.S. Cl.
USPC .......................................... 623/1.22; 623/1.2
(58) Field of Classification Search
USPC ........................................ 623/1.22, 1.23, 1.2
See application file for complete search history.

(56) References Cited

U.S. PATENT DOCUMENTS

| | | | |
|---|---|---|---|
| 5,091,205 A | 2/1992 | Fan | |
| 5,464,419 A | 11/1995 | Glastra | |
| 5,527,353 A | 6/1996 | Schmitt | |
| 5,591,223 A | 1/1997 | Lock et al. | |

(Continued)

FOREIGN PATENT DOCUMENTS

| DE | 04130431 A1 | 3/1993 |
|---|---|---|
| DE | 29621207 U1 | 1/1997 |

(Continued)

OTHER PUBLICATIONS

U.S. Appl. No. 10/362,040, filed Jun. 27, 2003 Office Action dated Jan. 10, 2006.

(Continued)

*Primary Examiner* — Gregory Anderson
(74) *Attorney, Agent, or Firm* — Rutan & Tucker, LLP

(57) ABSTRACT

Preferred embodiments of an implantable medical device with a high degree of flexibility is shown and described. One aspect includes an implantable stent having an intermediate portion with a helical winding and first and second end portions. The implantable stent further includes a coupling portion with a helical winding, and bridges joining struts of defining the helical windings. The stent also includes a paddle providing a bridge joining the ends or the helical windings. Another aspect relates to a radially self-expansible stent with a plurality of radiopaque markers attached to it. The markers are shaped and located at the stent end such that the compressive stress exerted on the end annulus of the stent during release of the stent is shared between the markers and the inflection zones that do not carry a marker.

18 Claims, 17 Drawing Sheets

U.S. PATENT DOCUMENTS

| | | |
|---|---|---|
| 5,645,532 A | 7/1997 | Horgan |
| 5,725,572 A | 3/1998 | Lam et al. |
| 5,741,327 A | 4/1998 | Frantzen |
| 5,759,192 A | 6/1998 | Saunders |
| 5,800,511 A | 9/1998 | Mayer |
| 5,824,042 A | 10/1998 | Lombardi et al. |
| 5,824,059 A | 10/1998 | Wijay |
| 5,824,077 A | 10/1998 | Mayer |
| 5,843,118 A | 12/1998 | Sepetka et al. |
| 5,858,556 A | 1/1999 | Eckert et al. |
| 5,861,027 A | 1/1999 | Trapp |
| 5,868,783 A | 2/1999 | Tower |
| 5,922,020 A | 7/1999 | Klein et al. |
| 6,022,374 A | 2/2000 | Imran |
| 6,053,940 A | 4/2000 | Wijay |
| 6,056,187 A | 5/2000 | Acciai et al. |
| 6,086,611 A | 7/2000 | Duffy et al. |
| 6,099,561 A | 8/2000 | Alt |
| 6,174,329 B1 | 1/2001 | Callol et al. |
| 6,241,762 B1 | 6/2001 | Shanley |
| 6,270,524 B1 | 8/2001 | Kim |
| 6,293,966 B1 | 9/2001 | Frantzen |
| 6,334,871 B1 | 1/2002 | Dor et al. |
| 6,355,057 B1 | 3/2002 | DeMarais et al. |
| 6,379,381 B1 | 4/2002 | Hossainy et al. |
| 6,387,123 B1 | 5/2002 | Jacobs et al. |
| 6,409,752 B1 | 6/2002 | Boatman et al. |
| 6,451,047 B2 | 9/2002 | McCrea et al. |
| 6,471,721 B1 | 10/2002 | Dang |
| 6,475,233 B2 | 11/2002 | Trozera |
| 6,478,816 B1 | 11/2002 | Kveen et al. |
| 6,540,777 B2 | 4/2003 | Stenzel et al. |
| 6,547,818 B1 | 4/2003 | Rourke et al. |
| 6,562,065 B1 | 5/2003 | Shanley |
| 6,585,757 B1 | 7/2003 | Callol |
| 6,605,110 B2 | 8/2003 | Harrison |
| 6,629,994 B2 | 10/2003 | Gomez et al. |
| 6,676,700 B1 | 1/2004 | Jacobs et al. |
| 6,770,089 B1 | 8/2004 | Hong et al. |
| 6,797,217 B2 | 9/2004 | McCrea et al. |
| 6,827,734 B2 | 12/2004 | Fariabi |
| 6,878,162 B2 | 4/2005 | Bales et al. |
| 6,979,346 B1 | 12/2005 | Hossainy et al. |
| 7,060,093 B2 | 6/2006 | Dang et al. |
| 7,135,038 B1 | 11/2006 | Limon |
| 7,175,654 B2 | 2/2007 | Bonsignore et al. |
| 7,462,190 B2 | 12/2008 | Lombardi |
| 7,468,071 B2 | 12/2008 | Edwin et al. |
| 7,479,157 B2 | 1/2009 | Weber et al. |
| 7,691,461 B1 | 4/2010 | Prabhu |
| 7,771,463 B2 * | 8/2010 | Ton et al. ............... 623/1.11 |
| 7,772,659 B2 | 8/2010 | Rodmacq et al. |
| 8,043,364 B2 | 10/2011 | Lombardi et al. |
| 8,152,842 B2 | 4/2012 | Schlun |
| 2002/0007212 A1 | 1/2002 | Brown et al. |
| 2002/0116044 A1 | 8/2002 | Cottone et al. |
| 2002/0116051 A1 | 8/2002 | Cragg |
| 2002/0138136 A1 | 9/2002 | Chandresekaran et al. |
| 2002/0193867 A1 | 12/2002 | Gladdish et al. |
| 2002/0193869 A1 | 12/2002 | Dang |
| 2002/0198589 A1 | 12/2002 | Leong |
| 2003/0055485 A1 | 3/2003 | Lee et al. |
| 2003/0135254 A1 | 7/2003 | Curcio et al. |
| 2003/0144725 A1 | 7/2003 | Lombardi |
| 2003/0216807 A1 | 11/2003 | Jones et al. |
| 2003/0225448 A1 | 12/2003 | Gerberding |
| 2004/0015228 A1 | 1/2004 | Lombardi et al. |
| 2004/0015229 A1 | 1/2004 | Fulkerson et al. |
| 2004/0034402 A1 | 2/2004 | Bales et al. |
| 2004/0044401 A1 | 3/2004 | Bales et al. |
| 2004/0073290 A1 | 4/2004 | Chouinard |
| 2004/0073291 A1 | 4/2004 | Brown et al. |
| 2004/0117002 A1 | 6/2004 | Girton et al. |
| 2004/0230293 A1 | 11/2004 | Yip et al. |
| 2004/0236400 A1 | 11/2004 | Edwin et al. |
| 2004/0236409 A1 | 11/2004 | Pelton et al. |
| 2004/0254637 A1 | 12/2004 | Yang et al. |
| 2005/0049682 A1 | 3/2005 | Leanna et al. |
| 2005/0060025 A1 | 3/2005 | Mackiewicz et al. |
| 2005/0149168 A1 | 7/2005 | Gregorich |
| 2005/0172471 A1 | 8/2005 | Vietmeier |
| 2005/0182477 A1 | 8/2005 | White |
| 2005/0222667 A1 | 10/2005 | Hunt |
| 2005/0278019 A1 | 12/2005 | Gregorich |
| 2006/0030934 A1 | 2/2006 | Hogendijk et al. |
| 2006/0064153 A1 | 3/2006 | Langhans et al. |
| 2006/0216431 A1 | 9/2006 | Kerrigan |
| 2006/0241741 A1 | 10/2006 | Lootz |
| 2006/0265049 A1 | 11/2006 | Gray et al. |
| 2007/0112421 A1 | 5/2007 | O'Brien |
| 2007/0219624 A1 | 9/2007 | Brown et al. |
| 2008/0051885 A1 | 2/2008 | Llanos et al. |
| 2008/0188924 A1 | 8/2008 | Prabhu |
| 2009/0125092 A1 | 5/2009 | McCrea et al. |
| 2009/0125099 A1 | 5/2009 | Weber et al. |
| 2009/0200360 A1 | 8/2009 | Wack |
| 2009/0204201 A1 | 8/2009 | Wack |
| 2009/0204203 A1 | 8/2009 | Allen et al. |
| 2010/0016949 A1 | 1/2010 | Wack |
| 2010/0070021 A1 | 3/2010 | Wack et al. |
| 2010/0114298 A1 | 5/2010 | Dorn et al. |
| 2010/0191321 A1 | 7/2010 | Schlun et al. |
| 2010/0211161 A1 | 8/2010 | Dreher |
| 2010/0234936 A1 | 9/2010 | Schlun |
| 2010/0249903 A1 | 9/2010 | Wack et al. |
| 2010/0298921 A1 | 11/2010 | Schlun et al. |
| 2011/0196473 A1 | 8/2011 | Mccrea et al. |
| 2011/0198327 A1 | 8/2011 | Prabhu |
| 2011/0245905 A1 | 10/2011 | Weber et al. |
| 2011/0319977 A1 | 12/2011 | Pandelidis et al. |
| 2012/0041542 A1 | 2/2012 | Lombardi et al. |

FOREIGN PATENT DOCUMENTS

| | | |
|---|---|---|
| DE | 19728337 A1 | 1/1999 |
| DE | 29904817 U1 | 5/1999 |
| DE | 10201151 A1 | 7/2003 |
| DE | 202004014789 U1 | 1/2005 |
| DE | 102004045994 A1 | 3/2006 |
| EP | 0481365 A1 | 4/1992 |
| EP | 0709068 A2 | 5/1996 |
| EP | 0800800 A1 | 10/1997 |
| EP | 0847733 A1 | 6/1998 |
| EP | 0870483 A2 | 10/1998 |
| EP | 1029517 A2 | 8/2000 |
| EP | 1034751 A2 | 9/2000 |
| EP | 1157673 A2 | 11/2001 |
| EP | 1190685 A2 | 3/2002 |
| EP | 1212991 A2 | 6/2002 |
| EP | 1245203 A2 | 10/2002 |
| EP | 1255507 A1 | 11/2002 |
| EP | 1356789 A1 | 10/2003 |
| EP | 1433438 A2 | 6/2004 |
| EP | 1488763 A2 | 12/2004 |
| EP | 1767240 A1 | 3/2007 |
| EP | 2134301 A2 | 12/2009 |
| FR | 2626046 A1 | 7/1989 |
| GB | 453944 A | 9/1936 |
| JP | 07315147 A | 12/1995 |
| JP | 4827965 B2 | 11/2011 |
| JP | 4933018 B2 | 5/2012 |
| WO | 9417754 A1 | 8/1994 |
| WO | 9503010 A1 | 2/1995 |
| WO | 9626689 A1 | 9/1996 |
| WO | 9733534 A1 | 9/1997 |
| WO | 9820810 A1 | 5/1998 |
| WO | 9915108 A2 | 4/1999 |
| WO | 9938457 A1 | 8/1999 |
| WO | 9949928 A1 | 10/1999 |
| WO | 9955253 A1 | 11/1999 |
| WO | 0045742 A1 | 8/2000 |
| WO | 0049601 A1 | 8/2000 |
| WO | 0064375 A1 | 11/2000 |
| WO | 0101889 A1 | 1/2001 |
| WO | 0132102 A1 | 5/2001 |
| WO | 0158384 A1 | 8/2001 |
| WO | 0176508 A2 | 10/2001 |
| WO | 0215820 A2 | 2/2002 |

| | | | |
|---|---|---|---|
| WO | 0249544 A1 | 6/2002 |
| WO | 03055414 A1 | 7/2003 |
| WO | 03075797 | 9/2003 |
| WO | 03101343 A1 | 12/2003 |
| WO | 2004019820 A1 | 3/2004 |
| WO | 2004028408 A1 | 4/2004 |
| WO | 2004032802 A2 | 4/2004 |
| WO | 2004058384 A1 | 7/2004 |
| WO | 2005067816 A1 | 7/2005 |
| WO | 2005072652 A1 | 8/2005 |
| WO | 2005104991 A1 | 11/2005 |
| WO | 2006010636 A1 | 2/2006 |
| WO | 2006010638 A1 | 2/2006 |
| WO | 2006014768 A1 | 2/2006 |
| WO | 2006025847 A2 | 3/2006 |
| WO | WO-2006026778 | 3/2006 |
| WO | 2006036912 A2 | 4/2006 |
| WO | 2006047977 A1 | 5/2006 |
| WO | 2006064153 A1 | 6/2006 |
| WO | 2007073413 A1 | 6/2007 |
| WO | 2007131798 A1 | 11/2007 |
| WO | 2007135090 A1 | 11/2007 |
| WO | 2008006830 A1 | 1/2008 |
| WO | 2008022949 A1 | 2/2008 |
| WO | 2008022950 A1 | 2/2008 |
| WO | 2008025762 A1 | 3/2008 |
| WO | 2008028964 A2 | 3/2008 |
| WO | 2008055980 A1 | 5/2008 |
| WO | 2008068279 A1 | 6/2008 |
| WO | 2008101987 A1 | 8/2008 |
| WO | 2008119837 A2 | 10/2008 |
| WO | 2009030748 A2 | 3/2009 |

OTHER PUBLICATIONS

U.S. Appl. No. 10/362,040, filed Jun. 27, 2003 Office Action dated Jul. 15, 2009.
U.S. Appl. No. 10/362,040, filed Jun. 27, 2003 Office Action dated Jun. 23, 2005.
U.S. Appl. No. 10/362,040, filed Jun. 27, 2003 Office Action dated Jun. 5, 2007.
U.S. Appl. No. 12/300,985, filed Aug. 6, 2010 Final Office Action dated Aug. 15, 2012.
U.S. Appl. No. 12/300,985, filed Aug. 6, 2010 Non-Final Office Action dated Mar. 15, 2012.
U.S. Appl. No.12/301,019, filed Feb. 2, 2009 Advisory Action dated Apr. 27, 2011.
U.S. Appl. No.12/301,019, filed Feb. 2, 2009 Final Office Action dated Feb. 7, 2011.
U.S. Appl. No. 12/301,019, filed Feb. 2, 2009 Non-Final Office Action dated Sep. 3, 2010.
U.S. Appl. No. 12/373,116, filed Jul. 14, 2009 Advisory Action dated Jul. 26, 2011.
U.S. Appl. No. 12/373,116, filed Jul. 14, 2009 Final Office Action dated Apr. 27, 2011.
U.S. Appl. No. 12/373,116, filed Jul. 14, 2009 Final Office Action dated Mar. 29, 2012.
U.S. Appl. No. 12/373,116, filed Jul. 14, 2009 Non-Final Office Action dated Nov. 10, 2010.
U.S. Appl. No. 12/373,116, filed Jul. 14, 2009 Non-Final Office Action dated Nov. 18, 2011.
U.S. Appl. No. 12/373,116, filed Jul. 14, 2009 Notice of Panel Decision dated Aug. 20, 2012.
U.S. Appl. No. 12/438,102, filed Feb. 19, 2009 Non-Final Office Action dated Nov. 15, 2010.
U.S. Appl. No. 12/438,330, filed Feb. 20, 2009 Advisory Action dated Oct. 14, 2010.
U.S. Appl. No. 12/438,330, filed Feb. 20, 2009 Advisory Action dated Oct. 20, 2011.
U.S. Appl. No. 12/438,330, filed Feb. 20, 2009 Final Office Action dated Aug. 11, 2011.
U.S. Appl. No. 12/438,330, filed Feb. 20, 2009 Non-Final Office Action dated Jun. 7, 2012.
U.S. Appl. No. 12/438,330, filed Feb. 20, 2009 Notice of Allowance dated Sep. 25, 2012.
U.S. Appl. No. 12/438,330, filed Feb. 20, 2009 Office Action dated Aug. 5, 2010.
U.S. Appl. No. 12/438,330, filed Feb. 20, 2009 Office Action dated Mar. 16, 2010.
U.S. Appl. No. 12/438,330, filed Feb. 20, 2009 Office Action dated Mar. 4, 2011.
U.S. Appl. No. 12/438,527, filed Feb. 23, 2009 Advisory Action dated May 24, 2012.
U.S. Appl. No. 12/438,527, filed Feb. 23, 2009 Final Office Action dated Mar. 7, 2012.
U.S. Appl. No. 12/438,527, filed Feb. 23, 2009 Non-Final Office Action dated Jul. 11, 2011.
U.S. Appl. No. 12/514,177, filed May 8, 2009 Advisory Action dated Sep. 10, 2012.
U.S. Appl. No. 12/514,177, filed May 8, 2009 Final Office Action dated Apr. 27, 2011.
U.S. Appl. No. 12/514,177, filed May 8, 2009 Final Office Action dated Jul. 11, 2012.
U.S. Appl. No. 12/514,177, filed May 8, 2009 Non-Final Office Action dated Jan. 5, 2011.
U.S. Appl. No. 12/514,177, filed May 8, 2009 Non-Final Office Action dated Mar. 13, 2012.
U.S. Appl. No. 12/517,096, filed Jun. 1, 2009 Final Office Action dated Oct. 31, 2011.
U.S. Appl. No. 12/517,096, filed Jun. 1, 2009 Non-Final Office Action dated Jun. 18, 2012.
U.S. Appl. No. 12/517,096, filed Jun. 1, 2009 Non-Final Office Action dated May 6, 2011.
U.S. Appl. No. 12/517,096, filed Jun. 1, 2009 Notice of Panel Decision dated Mar. 23, 2012.
U.S. Appl. No. 12/528,289, filed Aug. 26, 2009 Non-Final Office Action dated Jan. 27, 2012.
U.S. Appl. No. 12/594,531, filed Oct. 2, 2009 Advisory Action dated Jan. 10, 2012.
U.S. Appl. No. 12/594,531, filed Oct. 2, 2009 Final Office Action dated Nov. 4, 2011.
U.S. Appl. No. 12/594,531, filed Oct. 2, 2009 Non-Final Office Action dated Dec. 17, 2010.
U.S. Appl. No. 12/594,531, filed Oct. 2, 2009 Non-Final Office Action dated May 12, 2011.
U.S. Appl. No. 12/594,531, filed Oct. 2, 2009 Non-Final Office Action dated Oct. 2, 2012.
Database Wikipedia, Sep. 11, 2007, "Lumen (anatomy)" XP 002453737 abstract.
EP 07787316.4 filed Jul. 10, 2007 Examination Report dated Dec. 23, 2011.
EP 07802603.6 filed Aug. 14, 2007 Office Action dated Dec. 13, 2010.
EP 07820066.4 filed Mar. 31, 2009 Examination Report dated Dec. 27, 2011.
EP 09177588 filed Aug. 14, 2007 Search Report dated Aug. 12, 2011.
EP 12174308.2 filed Apr. 3, 2008 European Search Report dated Sep. 10, 2012.
PCT/EP2001/009467 International Preliminary Examination Report Sep. 17, 2002.
PCT/EP2001/009467 International Search Report dated Feb. 18, 2002.
PCT/EP2007/004407 filed May 16, 2007 International Preliminary Report on Patentability dated Sep. 29, 2008.
PCT/EP2007/004407 filed May 16, 2007 Search Report dated Sep. 26, 2007.
PCT/EP2007/004407 filed May 16, 2007 Written Opinion dated Sep. 26, 2007.
PCT/EP2007/054822 filed on May 18, 2007 International Preliminary Report on Patentability dated Nov. 18, 2008.
PCT/EP2007/054822 filed on May 18, 2007 Search Report dated Sep. 18, 2007.
PCT/EP2007/054822 filed on May 18, 2007 Written Opinion dated Nov. 18, 2008.
PCT/EP2007/057041 filed Jul. 10, 2007 International Preliminary Report on Patentability dated Jan. 13, 2009.
PCT/EP2007/057041 filed Jul. 10, 2007 International Search Report dated Oct. 18, 2007.

PCT/EP2007/057041 filed Jul. 10, 2007 Written Opinion Jan. 10, 2009.
PCT/EP2007/058415 filed on Aug. 14, 2007 International Preliminary Report on Patentability dated Feb. 24, 2009.
PCT/EP2007/058415 filed on Aug. 14, 2007 Search Report dated Nov. 30, 2007.
PCT/EP2007/058415 filed on Aug. 14, 2007 Written Opinion dated Nov. 30, 2007.
PCT/EP2007/058416 filed Aug. 14, 2007 International Preliminary Report on Patentability dated Feb. 24, 2009.
PCT/EP2007/058416 filed Aug. 14, 2007 International Search Report dated Nov. 22, 2007.
PCT/EP2007/058416 filed Aug. 14, 2007 Written Opinion dated Feb. 23, 2009.
PCT/EP2007/058912 filed on Aug. 28, 2007 International Preliminary Report on Patentability dated Nov. 5, 2008.
PCT/EP2007/058912 filed on Aug. 28, 2007 Search Report dated Nov. 12, 2007.
PCT/EP2007/058912 filed on Aug. 28, 2007 Written Opinion dated Nov. 12, 2007.
PCT/EP2007/059407 filed Sep. 7, 2007 International Search Report dated Jul. 3, 2008.
PCT/EP2007/062155 filed on Nov. 9, 2007 Search Report dated Mar. 12, 2008.
PCT/EP2007/062155 filed on Nov. 9, 2007 Written Opinion dated Mar. 12, 2009.
PCT/EP2007/062155 filed on Novermber 9, 2007 International Preliminary Report on Patentability dated Oct. 15, 2008.
PCT/EP2007/063347 filed Dec. 5, 2007 Search Report dated Jun. 10, 2009.
PCT/EP2007/063347 filed Dec. 5, 2007 Written Opinion mailed Jun. 10, 2009.
PCT/EP2007/063347 filed on Dec. 5, 2007 Search Report mailed Feb. 4, 2008.
PCT/EP2008/052121 filed Feb. 21, 2008 International Preliminary Report on Patentability dated Aug. 26, 2009.
PCT/EP2008/052121 filed Feb. 21, 2008 International Search Report dated May 19, 2008.
PCT/EP2008/052121 filed Feb. 21, 2008 Written Opinion dated May 9, 2008.
PCT/EP2008/054007 filed Apr. 3, 2008 International Preliminary Report on Patentability dated Jul. 27, 2009.
PCT/EP2008/054007 filed Apr. 3, 2008 Search Report dated Jan. 30, 2009.
PCT/EP2008/054007 filed Apr. 3, 2008 Written Opinion dated Jan. 30, 2009.
PCT/EP2008/061775 filed Sep. 5, 2008 International Search Report dated Apr. 22, 2009.
PCT/EP2008/061775 filed Sep. 5, 2008 Written Opinion dated Apr. 22, 2009.
U.S. Appl. No. 10/362,040, filed Jun. 27, 2003 Advisory Action dated Dec. 16, 2010.
U.S. Appl. No. 10/362,040, filed Jun. 27, 2003 Advisory Action dated Jan. 9, 2009.
U.S. Appl. No. 10/362,040, filed Jun. 27, 2003 Advisory Action dated Nov. 29, 2006.
U.S. Appl. No. 10/362,040, filed Jun. 27, 2003 Final Office Action dated Aug. 30, 2010.
U.S. Appl. No. 10/362,040, filed Jun. 27, 2003 Notice of Allowance dated Jun. 22, 2011.
U.S. Appl. No. 10/362,040, filed Jun. 27, 2003 Office Action dated Aug. 18, 2008.
U.S. Appl. No. 10/362,040, filed Jun. 27, 2003 Office Action dated Aug. 2, 2006.
U.S. Appl. No. 10/362,040, filed Jun. 27, 2003 Office Action dated Dec. 10, 2007.
U.S. Appl. No. 10/362,040, filed Jun. 27, 2003 Office Action dated Feb. 23, 2010.
Mar. 10, 2009 International Preliminary Report on Patentability and the Written Opinion of the International Searching Authority in international application PCT/EP2007/059047.

* cited by examiner

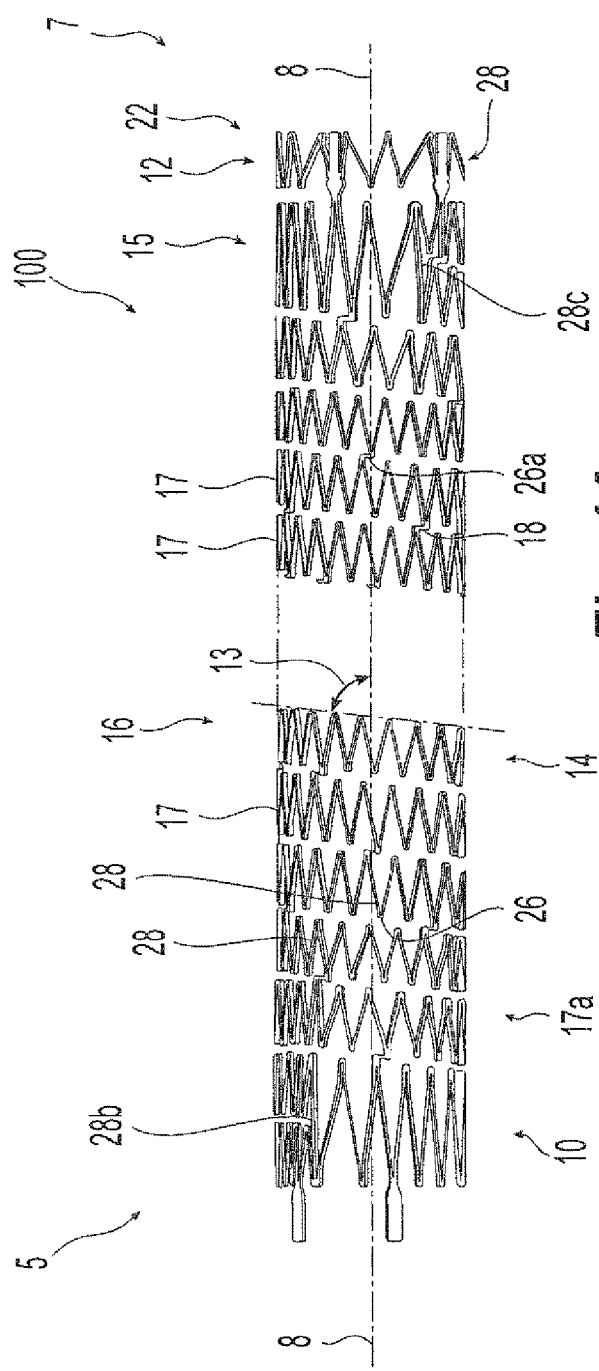
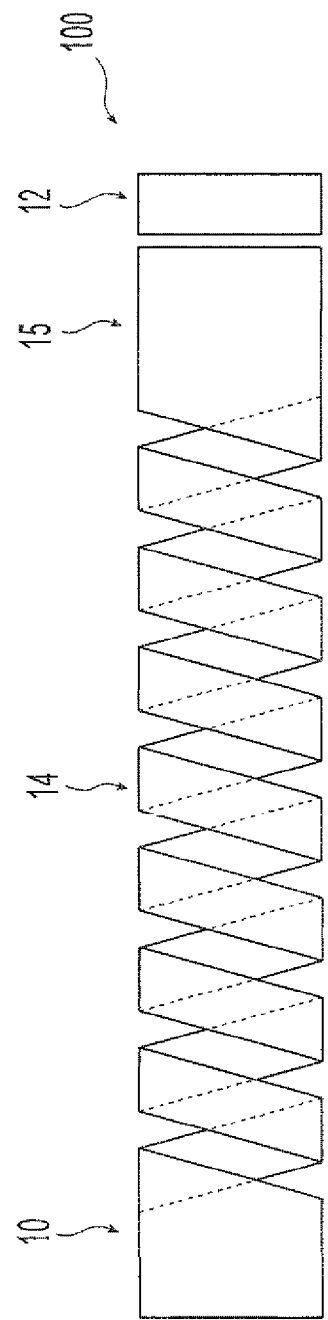
Fig. 1A
Fig. 1B

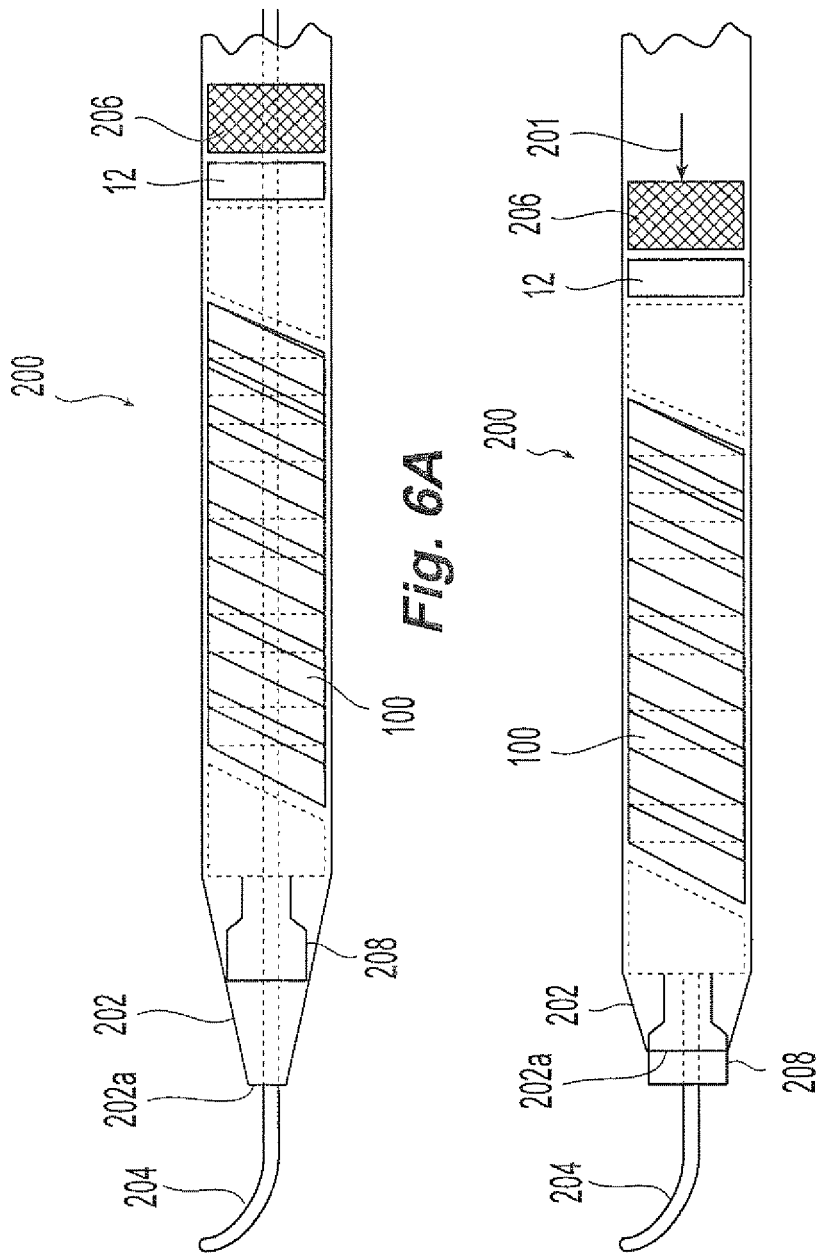

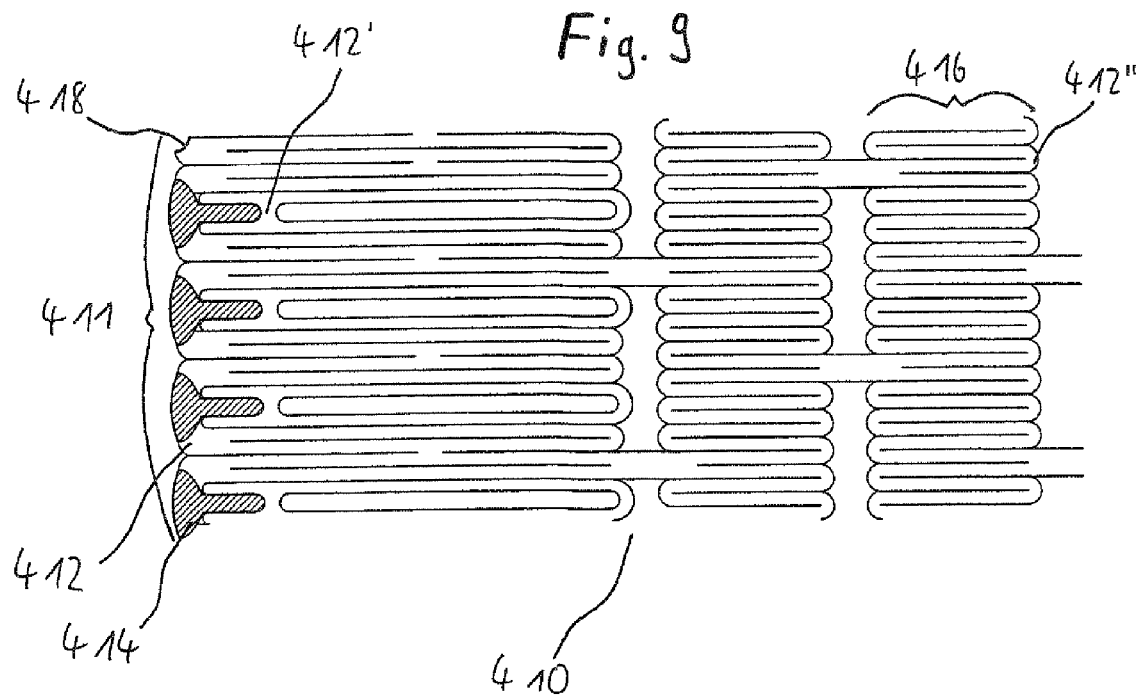
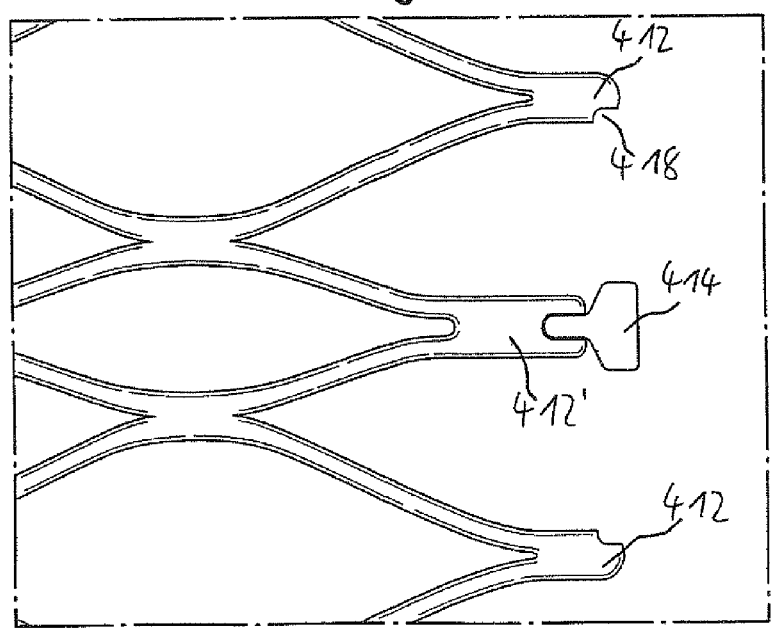

HELICAL IMPLANT HAVING DIFFERENT ENDS

RELATED APPLICATIONS

This application is a U.S. national stage application under 35 USC §371 of International Application No. PCT/EP2007/059407, filed Sep. 7, 2007, which claims benefit of priority to U.S. Provisional Patent Application No. 60/842,853, filed Sep. 7, 2006, each of which is incorporated by reference in its entirety into this application.

BACKGROUND

It is known in the medical field to utilize an implantable prosthesis to support a duct or vessel in a mammalian body. One such prosthesis may include a frame-like structure. Such frame-like structures are commonly known as a "stent", "stent-graft" or "covered stent." These structures are referred to collectively herein as a "stent", "implant", or an "implantable prosthesis."

The stent or prosthesis can be utilized to support a duct or vessel in the mammalian body that suffers from an abnormal widening (e.g., an aneurysm, vessel contraction or lesion such as a stenosis or occlusion), or an abnormal narrowing (e.g., a stricture). Stents are also utilized widely in the urethra, esophagus, biliary tract, intestines, arteries, veins, as well as peripheral vessels. The stent can be delivered via a small incision on a host body. Hence, the use of stents as a minimally-invasive surgical procedure has become widely accepted.

Previously developed stents for use in the biliary, venous, and arterial systems have been of two broad classes: balloon-expanded and self-expanding. In both of these classes, stents have been made by different techniques, including forming from wire and machining from a hollow tube. Such machining can be done by photo-chemical etching, laser-cutting, stamping, piercing, or other material-removal processes. Other manufacturing techniques have been proposed, such as vacuum or chemical deposition of material or forming a tube of machined flat material, but those "exotic" methods have not been widely commercialized.

One common form of stent is configured as a series of essentially identical rings connected together to form a lattice-like framework that defines a tubular framework. The series of rings may or may not have connecting linkages between the adjacent rings. One example does not utilize any connecting linkages between adjacent rings as it relies upon a direct connection from one ring to the next ring. It is believed that more popular examples utilize connecting linkages between adjacent rings, which can be seen in stent products offered by various companies in the marketplace.

All of the above stent examples utilize a biocompatible metal alloy (e.g., stainless steel, Nitinol or Elgiloy). The most common metal alloy utilized by these examples is Nitinol, which has strong shape memory characteristics so that the Nitinol self-expands when placed in the duct or vessel of a mammalian body at normal body temperature. In addition to self-expansion, these stents utilize a series of circular rings placed adjacent to each other to maintain an appropriate longitudinal spacing between each rings. Other examples are shown and described in U.S. Patent Publications 2004/0267353 and 2003/055485, and U.S. Pat. No. 5,824,059. Examples which use a helical configuration are shown and described, to identify a few, in U.S. Pat. Nos. 6,117,165; 6,488,703; 6,042,597; 5,906,639; 6,053,940; 6,013,854; 6,348,065; 6,923,828; 6,059,808; 6,238,409; 6,656,219; 6,053,940; 6,013,854; and 5,800,456. Examples that utilize a combination of helical and circular frameworks are shown and described in U.S. Patent Publications 2005/00033410; 2004/0158314; 2004/0158308; 2004/0186556, U.S. Pat. Nos. 6,969,402; 6,190,406, and WO 01/89421. All of the cited documents are hereby incorporated by reference in their entireties into this application.

A need is recognized for an implantable prosthesis device that maintains the patency of a vessel with the ability to adapt to the tortuous anatomy of the host by being highly flexible while being loadable into a delivery catheter of sufficiently small profile and easily deliverable to a target site in the vessel or duct by having the ability to navigate tortuous ducts or vessels.

BRIEF SUMMARY OF THE INVENTION

Accordingly, the present invention relates to various improvements of the structure of an implantable stent that embody a helical winding.

One aspect includes an implantable stent. The implantable stent includes an intermediate portion, first end portion, second end portion, and a coupling portion. The intermediate portion has a first continuous helical winding defining a plurality of circumferential sections circumscribing a longitudinal axis from a first end to a second end to define a portion of essentially a tube. The circumferential sections are spaced apart along the longitudinal axis. Each circumferential section has undulations disposed about a portion of the tube. The first end portion is disposed proximate the first end and has a second continuous helical winding that circumscribes a portion of the longitudinal axis. The second continuous helical winding has undulations of increasing lengths. The second end portion is disposed proximate the second end and has undulations that circumscribe the longitudinal axis to define a ring or a hoop. The coupling portion connects the second end portion to the intermediate portion and having a third continuous helical winding that circumscribes a portion of the longitudinal axis.

In another aspect of the implant stent, the stent includes a tubular intermediate portion defining a first helical winding and a longitudinal axis, a tubular end portion defining a different second helical winding and disposed adjacent to an end of the intermediate portion, and a paddle disposed adjacent to the end portion. The intermediate and end portions include a plurality of struts and bridges, with each strut having an end connected to an end of an adjacent strut, each bridge connected to an end of a strut, and the intermediate and end portions each having an end strut disposed proximate to an end of each helical winding. The paddle has a length and opposing ends disposed parallel to the longitudinal axis, an end of the paddle connected to a paddle strut connected to a paddle bridge, and one of the end struts connected to the paddle bridge. The stent can also have another one of the end struts connected to the paddle bridge, and at least one of the plurality of struts connected to the paddle bridge. The stent can also have another one of the end struts connected to the paddle strut, or another one of the end struts connected to the paddle. The stent can also have a ring portion disposed adjacent to the end portion, and another tubular end portion disposed at an opposing end of the intermediate portion that can define a third helical winding different from the first and second helical windings. The stent can also have another ring portion disposed adjacent to the another tubular end portion. The stent can also have another tubular end portion disposed at an opposing end of the intermediate portion, and a ring portion disposed adjacent to the another tubular end portion.

A method of delivering an implantable stent to a site in a vessel is provided. The method can be achieved by: providing an implantable stent in a delivery tubing that defines a longitudinal axis extending through the tubing and stent from a proximal end to a distal end and moving the tubing relative to the distal end of the stent. The implantable stent includes an intermediate portion having undulations circumscribing about and along the longitudinal axis to define a first continuous helical winding; a distal end portion having undulations circumscribing about and along the longitudinal axis to define a second continuous helical winding; a proximal end portion having undulations circumscribing the longitudinal axis to define an annular winding; and a coupling portion having undulations circumscribing about and along the longitudinal axis to define a third continuous helical winding.

These and other embodiments, features and advantages will become apparent to those skilled in the art when taken with reference to the following more detailed description of preferred embodiments of the invention in conjunction with the accompanying drawings that are first briefly described,

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 1A illustrates an embodiment of a helical type implantable stent in a truncated side view, with only the foreground structures shown and the rearward structures omitted for clarity.

FIG. 1B is a schematic side view of the structure of the implantable stent of FIG. 1A.

FIG. 6A illustrates the stent of FIG. 1A mounted in a delivery system.

FIG. 6B illustrates the stent of FIG. 1A mounted in a delivery system just prior to delivery of the stent via relative movement of the stent and an outer sheath.

FIG. 9 shows one end of a laser cutting of a stent with radiopaque markers attached to it, according to a second further preferred embodiment; and FIG. 10 shows a portion of the end annulus in the radially expanded state of the stent, according to a second further preferred embodiment.

DETAILED DESCRIPTION OF THE PREFERRED EMBODIMENTS

Figure 1C:
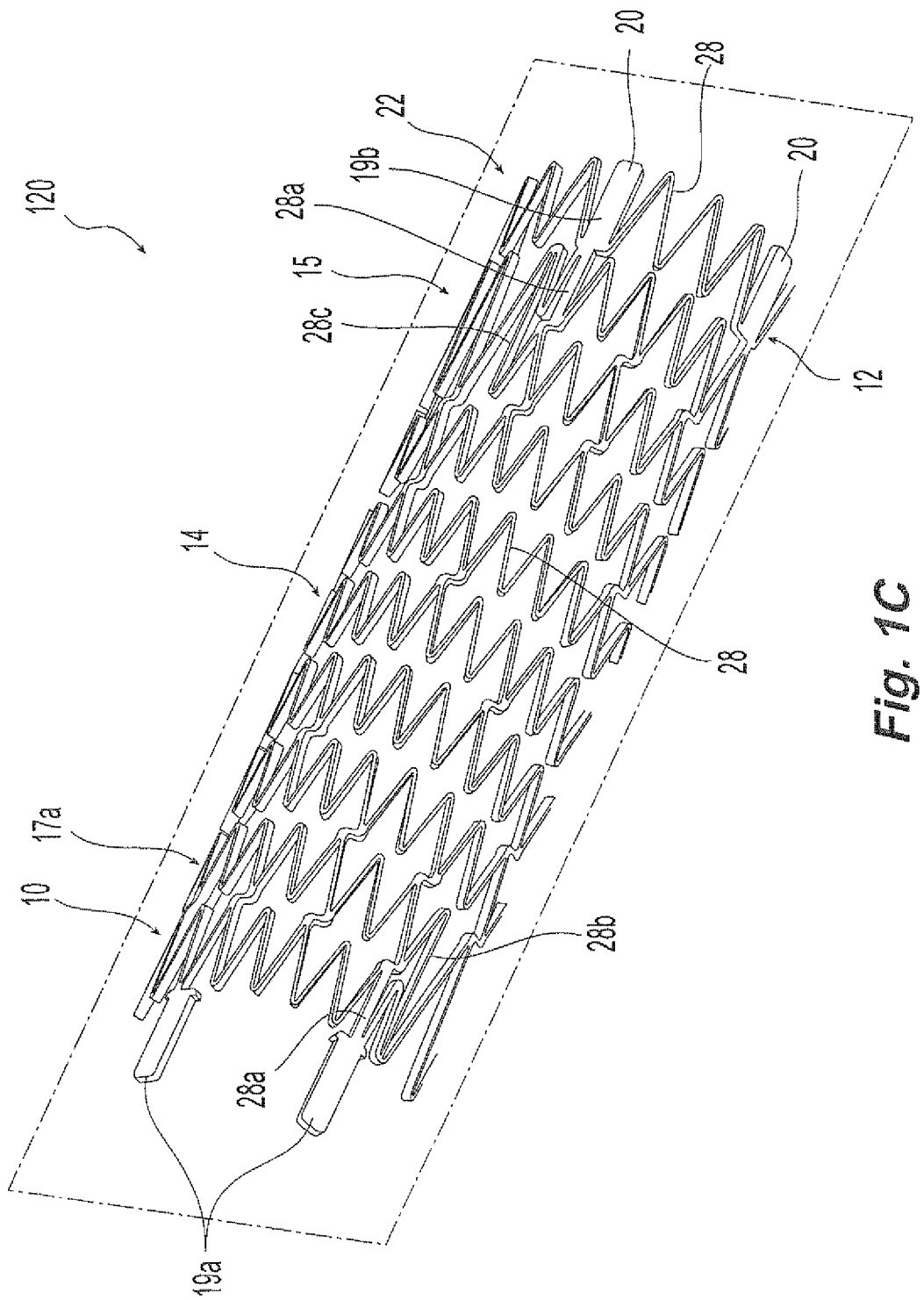
FIG. 1C is a perspective view of another embodiment of the stent of FIG. 1A, with a plane bisecting the stent so that only foreground structures are illustrated for clarity.

The following detailed description should be read with reference to the drawings, in which like elements in different drawings are identically numbered. The drawings, which are graphical representations and not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

FIGS. 1A-7B are graphical representations of various embodiments of the stent or its components, and a delivery system. Referring to FIGS. 1A and 1B, an implantable stent 100 is shown having a first end 5 and a second end 7 with first end portion 10, second end portion 12, an intermediate portion 14 and a coupling portion 15. The intermediate portion 14 includes a continuous helical winding 16. The winding 16 has a plurality of circumferential sections 17 that circumscribes a longitudinal axis 8 (with the continuation of each circumferential section shown in dashed lines in FIG. 1A) from the first end 5 to the second end 7 so as to define a portion of essentially a tube. The circumferential sections 17 are spaced apart along the longitudinal axis 8. Each circumferential section is disposed approximately 360 degrees about the longitudinal axis 8. Although only one helical winding 16 is shown, more that one helical winding can be used. For example, a helical winding with a first helical angle 13 with respect to the longitudinal axis 8 can be connected or coupled with another helical winding that has a different second helical angle.

The stent 100 includes at least one bridge 18 configured to connect one circumferential section 17 to an adjacent axially spaced circumferential section 17. The bridge 18 extends generally circumferentially on a plane generally orthogonal with respect to the longitudinal axis 8. That is, the bridge 18 forms a circumferential connector or bridge member (i.e., "circumferential bridge") between circumferential sections 17 of the helical winding 16. Preferably, there is a plurality of bridges 18 Interconnecting the circumferential sections 17. The stent 100 includes a plurality of struts 28, with some ends of two adjacent struts 28 engaging at a vertex 26. As shown in FIG. 1A, certain vertices 26a connect to the bridges 18.

Figure 1D:
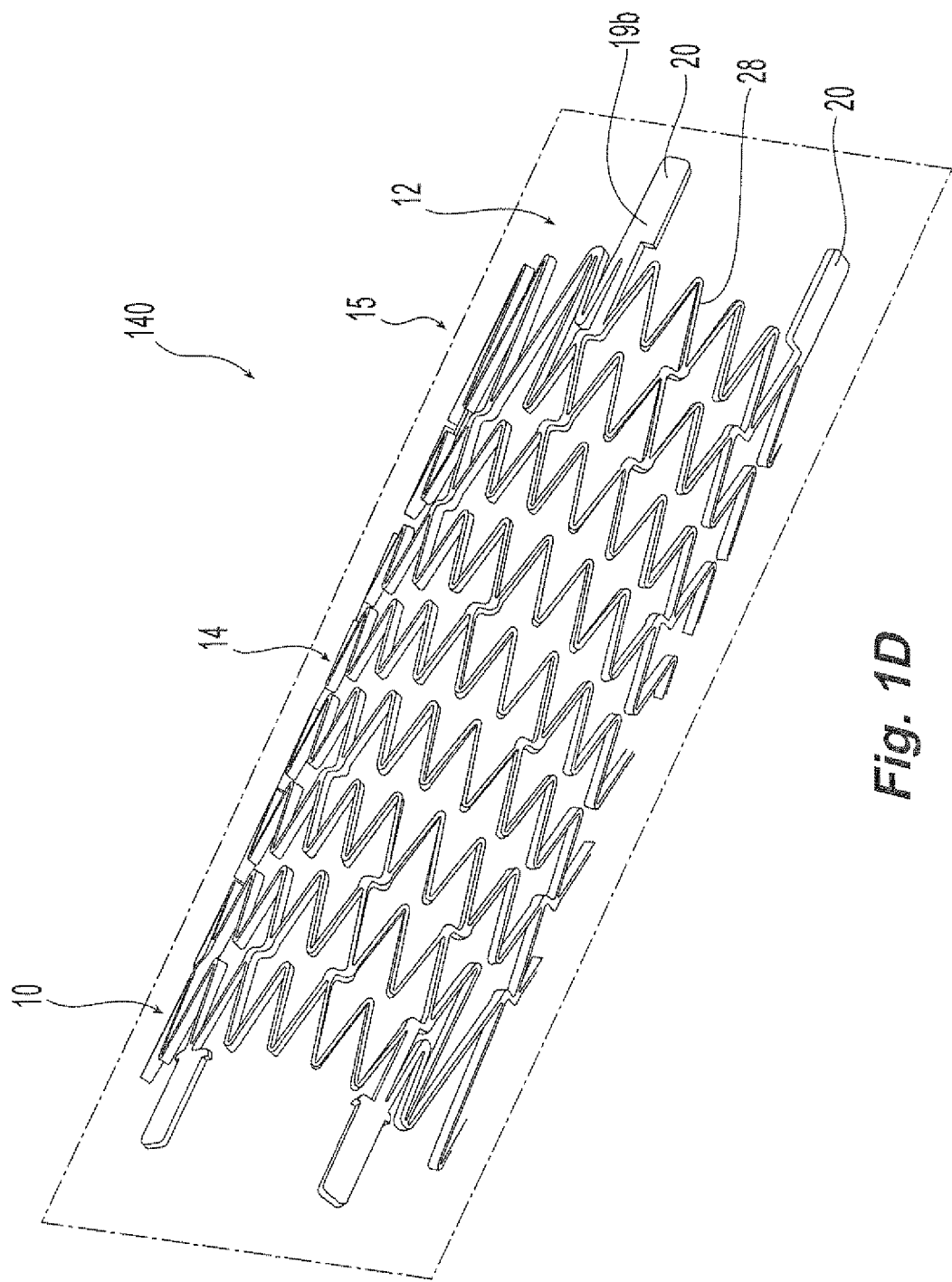
FIG. 1D is a perspective view of yet a further embodiment of the stent of FIG. 1C, with a plane bisecting the stent so that only foreground structures are illustrated for clarity.
Figure 1E:
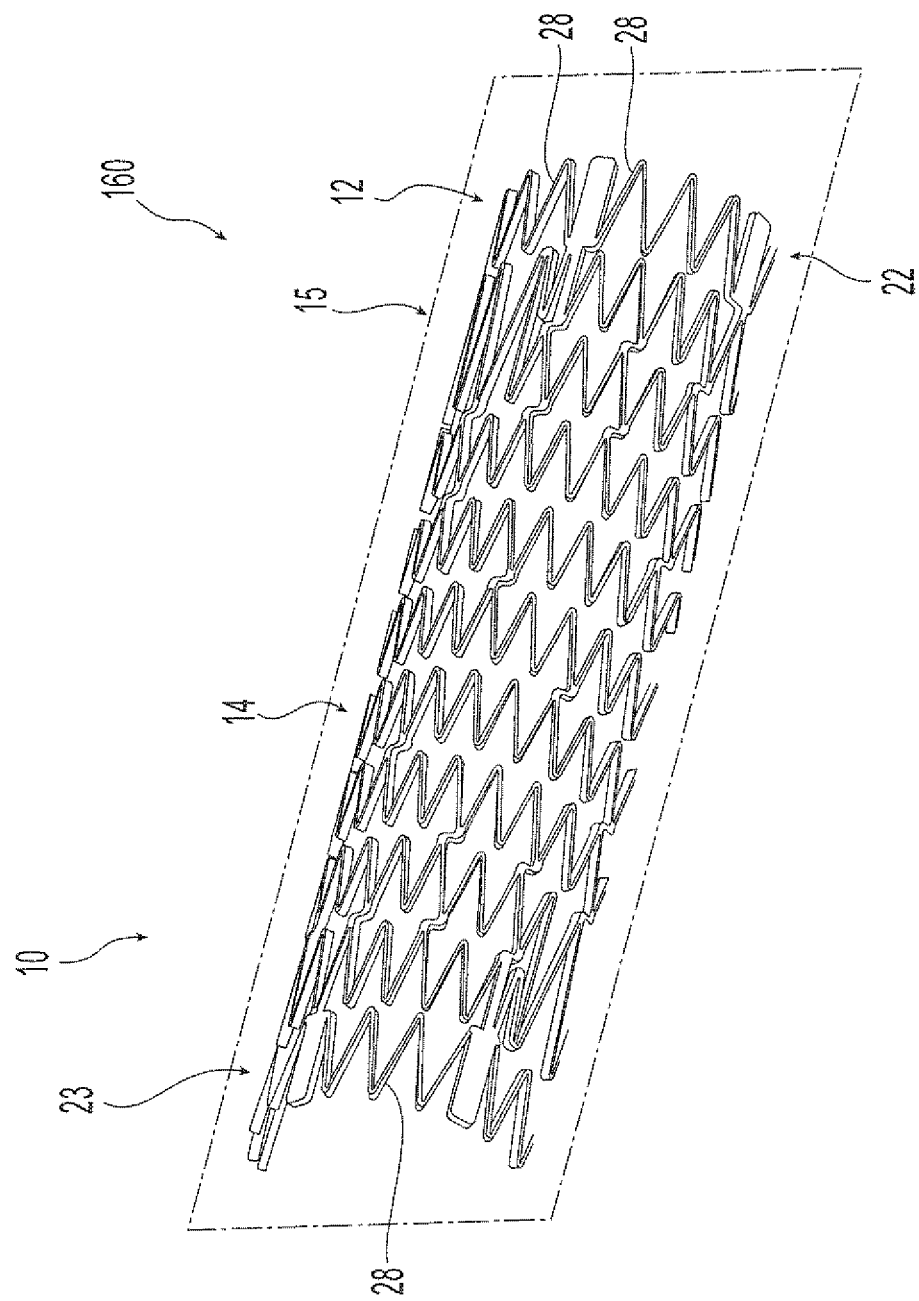
FIG. 1E is a perspective view of another embodiment of the stent of FIG. 1C, with a plane bisecting the stent so that only foreground structures are illustrated for clarity.
Figure 1F:
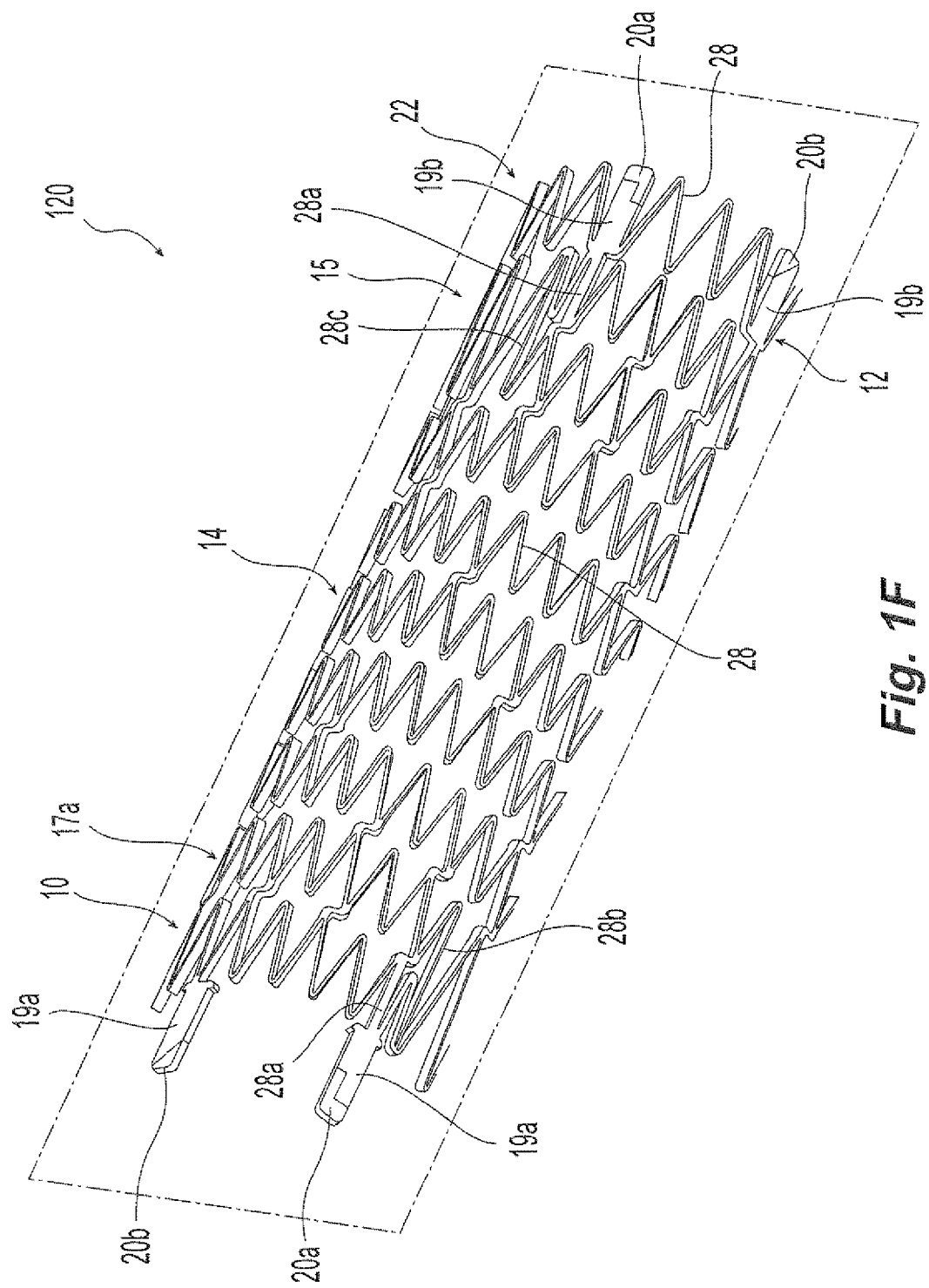
FIG. 1F is a perspective view of another embodiment of the stent of FIG. 1C, with a plane bisecting the stent so that only foreground structures are illustrated for FIG. 2 is a close-up view of a portion of one end of the stent of FIG. 1A in an unexpanded and unrolled configuration.

Variations of the stent 100 are possible but are not limited by the examples provided by the preferred embodiments. For example, in the stent 120 illustrated in FIG. 1C (with a plane bisecting the stent so that only foreground structures are illustrated), the stent 120 may have less than six paddles 19a and 19b and the cross-sectional areas of struts 28 (with the cross-section taken in a plane orthogonal to the axis 8) can be of different values. In FIG. 1C, the cross-sectional area of paddle struts 28a for stent 120 are larger than any other struts 28. In FIG. 1D, stent 140 can be provided without struts 28 in the second end portion 12. In FIG. 1E, for stent 160, the struts 28 can be used between the paddles 19a in the first end portion 10 to form an annular ring 23 similar to an annular ring 22 at the second end portion 12. In all of the variations for the stent 100, the cross-sectional area of each strut 28 of the end portions 10, 12, or 15 can be less than the cross-sectional area of each strut 28 of the intermediate portion 14 so as to provide for lower radial force, increased flexibility or a combination of both characteristics. Alternatively, the cross-sectional area of each strut 28 for each portion 10, 12, 14, or 15 can be altered so as to provide similar or varying radial force (i.e., a force developed by the structural framework radially away from the longitudinal axis 8) to support a lumen extending throughout the entire stent.

Figure 2:
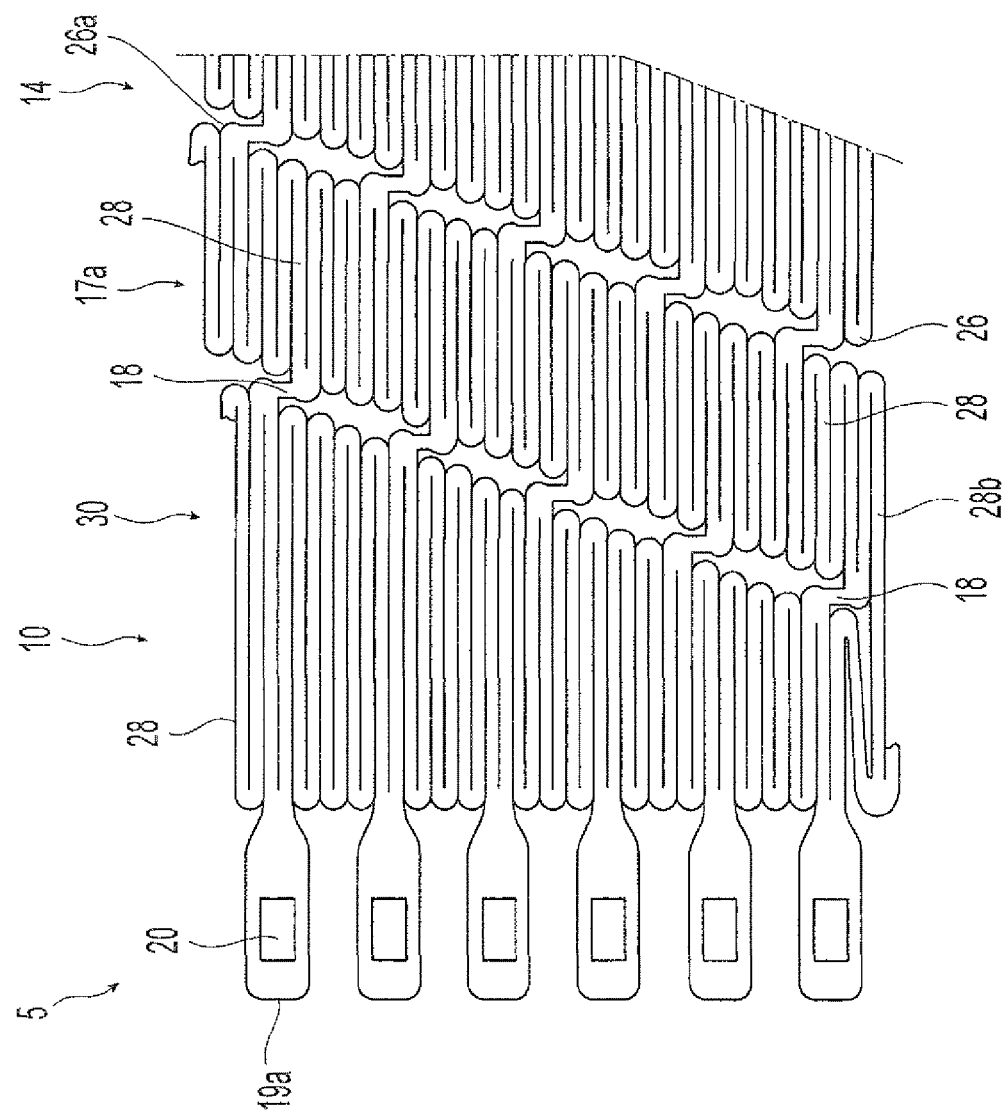
Figure 3:
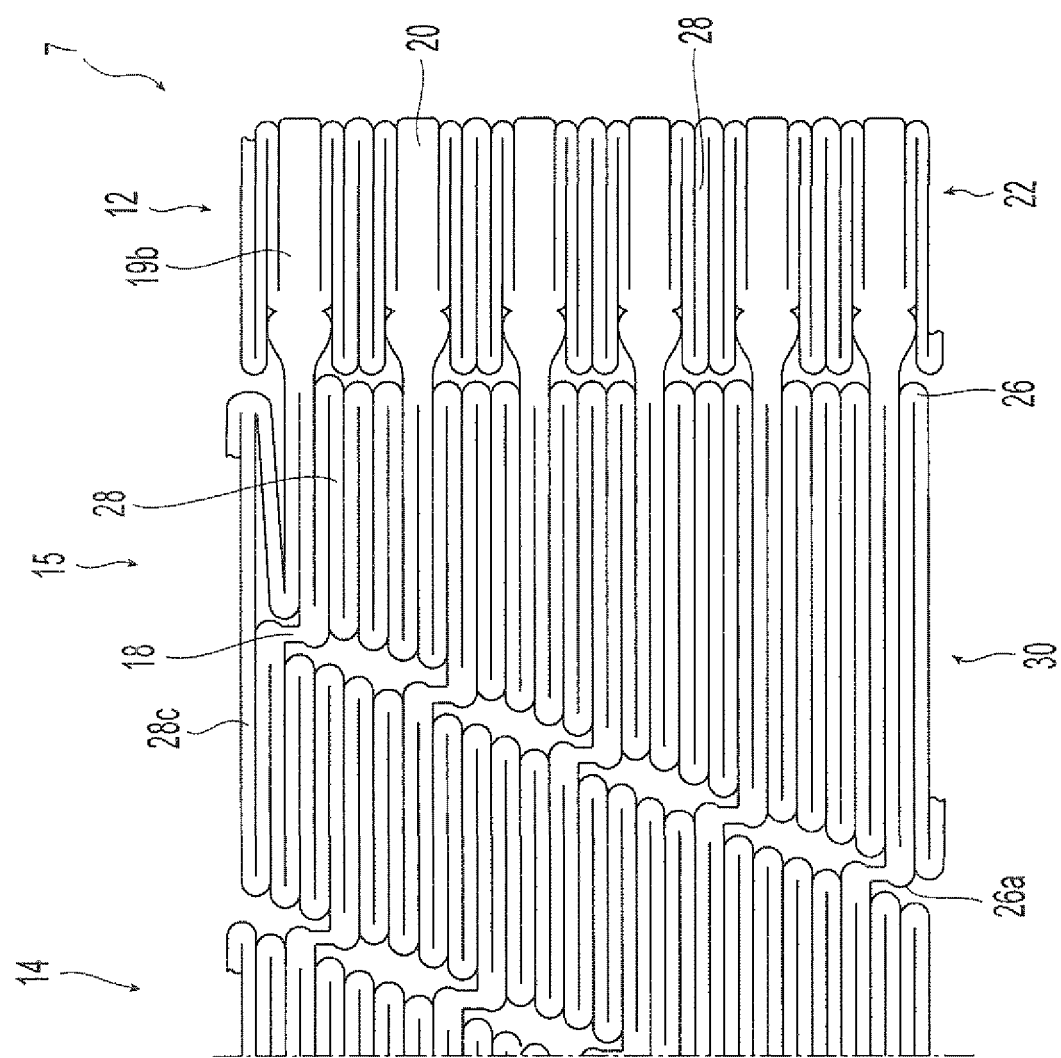
FIG. 3 is a close up view of a portion of the other end of the stent of FIG. 1A in an unexpanded and unrolled configuration.
Figure 4:
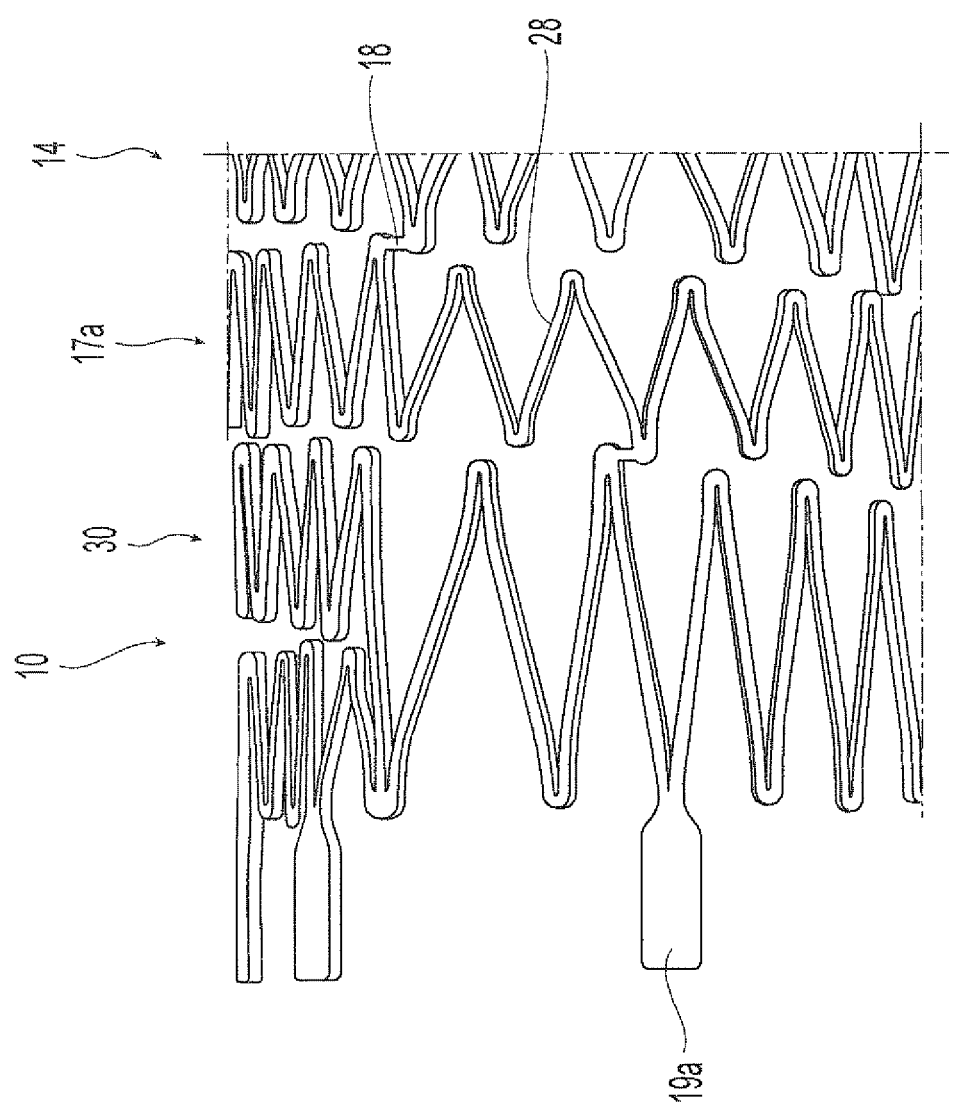
FIG. 4 is a close up view of a portion of the end of the stent of FIG. 2 in an expanded configuration.

Referring back to FIGS. 1A and 1C, the first and second end portions 10 and 12 are provided with dissimilar structural frameworks. Referring to FIGS. 2 and 3, respectively, the first end portion 10 includes paddles 19a while second end portion 12 includes paddles 19b which have a different shape. In FIGS. 2 and 4, first end portion 10 includes struts 28 with undulations 30 having increasing strut 28 lengths in the direction of the longitudinal axis 8 (in the unexpanded stent). The first end portion 10 is tied to the circumferential section 17a of intermediate portion 14 via bridges 18 with a connection strut 28b that connects the beginning of the undulations 30 of the first end portion 10 to the initial portion of circumferential section 17a (FIGS. 1A, 2, and 4). In other embodiments, there can be from one to ten struts 28 between every two bridges 18 depending on the flexibility desired in the first end 5, which can be increased with a lesser number of struts 28 between every two bridges 18 or decreased with a greater number of struts 28 between every two bridges 18. In the preferred embodiments, there are ten struts 28 between every two bridges 18 in the first end portion 10. In another preferred embodiment, there are four struts 28 disposed between every two bridges 18. The circumferential width of each strut 28 is preferably generally constant over the longitudinal length of the strut 28. The flexibility of the struts 28 in the first end 5 can be varied by varying the circumferential width or length of some struts 28. Moreover, the placement of the bridges 18 can also be utilized to vary the flexibility of the first end 5 such as, for example, by varying the distance between or the number of struts 28 disposed between the bridges 18 joining adjacent circumferential sections 17. The struts 28 of the first end portion 10 can also be utilized to connect the paddles 19a.

Referring to FIG. 3, the second end 7 is provided with two portions, second end portion 12 and coupling portion 15. The coupling portion 15 is provided with a connection strut 28c that ties the beginning of the coupling portion 15 to the second end portion 12 and the intermediate portion 14. The connection strut 28c is preferably a generally linear segment that ties both the intermediate portion 14 to the coupling portion 15. In the preferred embodiments, the connection strut 28c is generally diametrically opposed to the connection strut 28b. It is also preferable that the undulations 30 in coupling portion 15 include a plurality of struts 28 that extend in various lengths along the longitudinal axis 8 (in the unexpanded stent). In the preferred embodiments, there are ten struts 28 between every two bridges 18. In another preferred embodiment, there are four struts 28 between every two bridges 18. In other embodiments, there can be from one to ten struts 28 between every two bridges 18 depending on the flexibility desired in the second end 7, which can be increased with a lesser number of struts 28 between every two bridges 18 or decreased with a greater number of struts 28 between every two bridges 18. The circumferential width of each strut 28 preferably generally constant over the longitudinal length of the strut 28. The flexibility of the struts 28 in the second end 7 can be varied by varying the circumferential width or length of some struts 28. Moreover, the placement of the bridges 18 can also be utilized to vary the flexibility of the second end 7 such as, for example, by varying the distance between or the number of struts 28 disposed between the bridges 18 joining adjacent circumferential sections 17. The struts 28 of the second end portion 12 are utilized to connect the paddles 19b.

In the preferred embodiments, the undulations 30 are formed by generally linear struts 28, which are coupled to a vertex 26 of a strut 28 pair, which are deformed during expansion and compression of the stent. The undulations can have a sinusoidal shape, a zig-zag shape, form waves of varying amplitudes, or form waves of varying displacements, and combinations of these shapes. An extended portion 26a is formed the vertices 26 that are joined together with a bridge 18, so that deformations in the struts 28 connected to the vertex 26, resulting from the expansion or compression of the stent, do not fully transmit to the bridge 18, as illustrated in FIGS. 2 and 3. The stent can be made, for example, Nitinol, weak shape memory metals (e.g., stainless steel, platinum, Elgiloy), shape memory polymers, bioresorbable metals and polymers. Preferably, the stent is a Nitinol self-expanding stent of an approximately 6 mm fully-expanded diameter, the bridge 18 is approximately 100 microns wide (in the direction the longitudinal axis 8), approximately 200 microns thick (radial to the longitudinal axis 8), and approximately 130 microns long (in the circumferential direction). The struts 28 connecting to each bridge 18 shown in FIGS. 1A, 2, and 3 are preferably approximately 90 microns wide (in the circumferential direction), approximately 200 microns thick (radial to the longitudinal axis 8), and approximately 1500 microns long (in the direction of the longitudinal axis 8 in the unexpanded configuration).

Referring to FIG. 2, if the distortions of the stent are large enough, there can be interference between or overlapping of the markers 20. These distortions may arise during manufacture of the stent or when the pre-form of a self-expanded stent is expanded to its final size. Similar distortions may arise when a finished stent is compressed for insertion into a delivery system, or when the stent is In place in vivo but held in a partially-compressed shape by the anatomy.

As provided for herein, the distortions of the stent at the ends 5 and 7 may be reduced or virtually eliminated. Specifically, a connecting structure formed by an annular ring 22 in the second end portion 12 is provided for the second end 7 in FIG. 5A that includes a series of struts 28 and vertices 26 (similar to the struts 28 and vertices 26 in the intermediate portion 14) that are connected between adjacent paddles 19b in order to present reactive forces to resist expansion and compression of the struts. The connection of the struts 28 to the outer end 29 of the paddles 19b provides a leverage that maintains the longitudinal alignment of the paddles 19b while presenting radial compressive and expansion forces similar to that of the struts 28 in the intermediate portion 14. The struts 28 of the second end portion 12 are cut into the stent pre-form at the same time that the strut and bridge pattern for the rest of the stent is cut, typically using a laser cutting apparatus or by a suitable forming technique (e.g., etching or EDM). The struts 28 of the second end portion 12 tend to hold the paddles 19b (which may be coupled to markers 20) and their extensions in parallel or generally in longitudinal alignment when the stent pre-form is expanded during the manufacturing process. Strain relief portions 21 can be provided to allow for movement of the struts 28 during expansion.

Once the stent pre-form has been expanded, sacrificial struts (not shown) existing in the stent pre-form between facing vertices 26 of adjacent circumferential sections 17 may be either removed or left in place to form part of the finished stent. If it is desired to remove the sacrificial struts, then the sacrificial struts may be designed with notches or other weakening features where the sacrificial struts are attached, so that the sacrificial struts may be easily removed by cutting or breaking them at the connecting point.

Alternatively, the sacrificial struts may be designed so that they remain part of the stent. In this case, there would be no artificially weakened points. After the stent pre-form is expanded, the final manufacturing operations would be completed, including cleaning, heat-treating, deburring, polishing, and final cleaning or coating. The resulting stent may then have the sacrificial struts in place as an integral part of the stent structure.

Figure 5A:
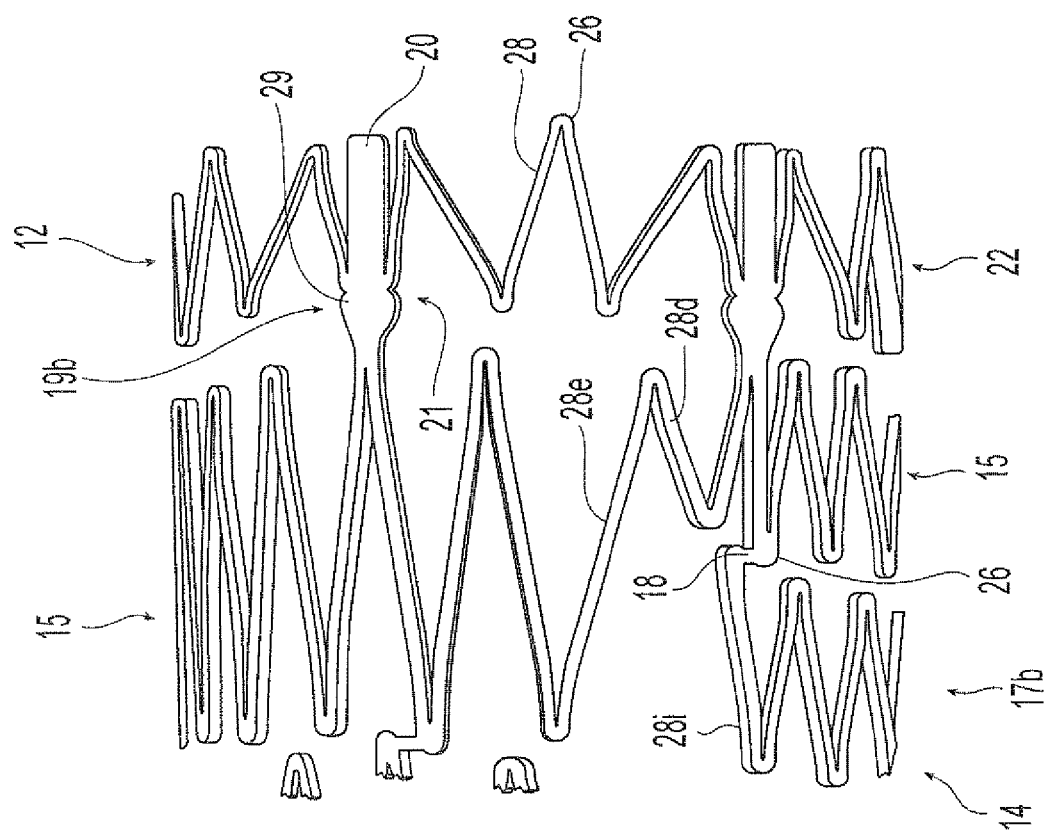
FIG. 5A illustrates a portion of an end of the stent of FIG. 3 in an expanded configuration.

In the embodiment shown in FIGS. 2 and 3, the markers 20 are approximately 620 microns wide (in the circumferential direction) and approximately 1200 microns long (in the longitudinal direction). Most preferably, the markers 20 are unitary with the paddles 19a and 19b, are generally rectangular in configuration, and may have the inside surface of each marker 20 curved to conform to the tubular inner surface of the helical winding 16. Alternatively, the markers 20 can be joined by welding, bonding, soldering or swaging to portions or ends of the paddles 19a/19b. In a further alternative, materials may be removed from either the luminal or abluminal surface of the paddles 19a/19b to provide a void, and a radiopaque material can be joined to or filled in the void. The markers 20 may be mounted at the end of paddles 19a/19b. The struts 28 joining the paddles 19a/19b may Include struts that are approximately 80 microns wide (in the circumferential direction) and approximately 1500 microns long (In the longitudinal direction). In the embodiment of FIGS. 3 and 5C, there are six struts 28 between two adjacent paddles 19b or markers 20. Preferably, the rectangular marker 20 may have a longitudinal length extending generally parallel to the longitudinal axis 8 and a circumferential width that is greater than two times the circumferential width of any strut 28. In one embodiment, the circumferential width of at least one strut 28 is approximately 65 microns and the circumferential width of the at least one strut 28 is approximately 80-150% of a width of a bridge 18 (in the direction of the longitudinal axis 8). In an alternative embodiment illustrated in FIG. 1F, a portion of paddles 19a or 19b can be removed and substituted with a stepped marker 20a or an angled marker 20b, or a marker of another geometry, with the marker 20a or 20b engaging the paddle 19a or 19b with a weld or another bonding technique. Alternatively, the paddles 19a or 19b can remain at their original lengths with only the ends modified to accept engagement with markers 20a or 20b, or extended to a longer length to engage markers 20a or 20b.

In an alternative embodiment, the annular ring 22 includes from two to eight struts 28 (instead of six as in the other embodiment) of approximately 90 microns wide (in the circumferential direction) and approximately 2000 microns long (in the direction of longitudinal axis 8). It should be noted that the more than four struts 28 can be utilized such as, for example, when no marker 20 is used or only a minimal number of markers 20 are needed. The markers 20 in the embodiments are approximately 620 microns wide (in the circumferential direction) and approximately 1200 microns long (in the direction of the longitudinal axis 8), and are mounted on paddles 19a/19b that are approximately 200 microns wide (in the circumferential direction) and approximately 2000 microns long (in the direction of the longitudinal axis 8). Preferably, the stent 100, in the form of a bare stent, can be manufactured from Nitinol tubing having a wall thickness of approximately 200 microns and an approximately 1730 micron outside diameter, and is designed to have an approximately 6 mm finished, expanded, and unimplanted outside diameter.

There are variations of the second end 7 of the stent 100. As shown in FIG. 5A, the connecting strut 28c (illustrated in FIG. 3) is eliminated so that there is one connection from the first end strut 28d and there is no direct connection from a terminal connecting strut 28e of the coupling portion 15 to the circumferential section 17b as in FIG. 5C. In contrast, as shown in FIG. 5C, the strut 28f is tied to both the circumferential section 17b of the intermediate portion 14 and the first end strut 28d of the coupling portion 15.

Figure 5B:
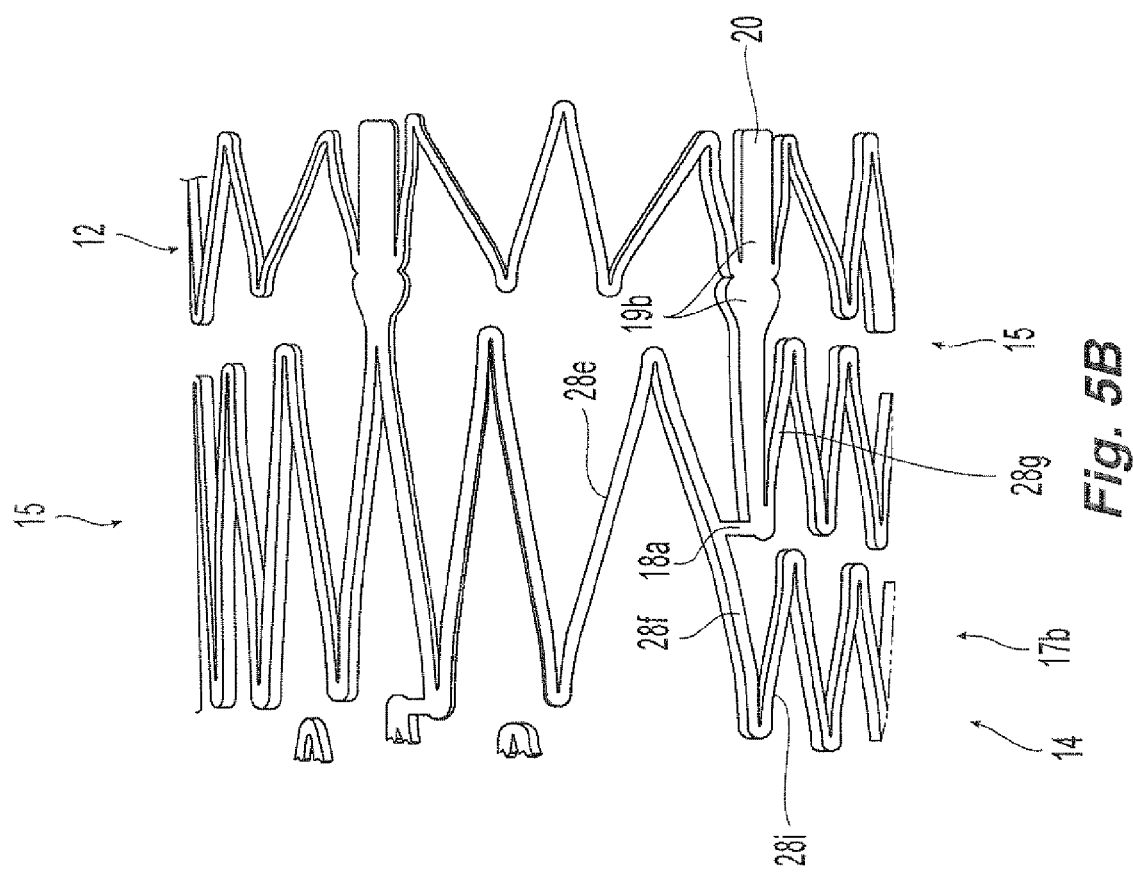
FIG. 5B illustrates a variation of the end portion of FIG. 5A.
Figure 5C:
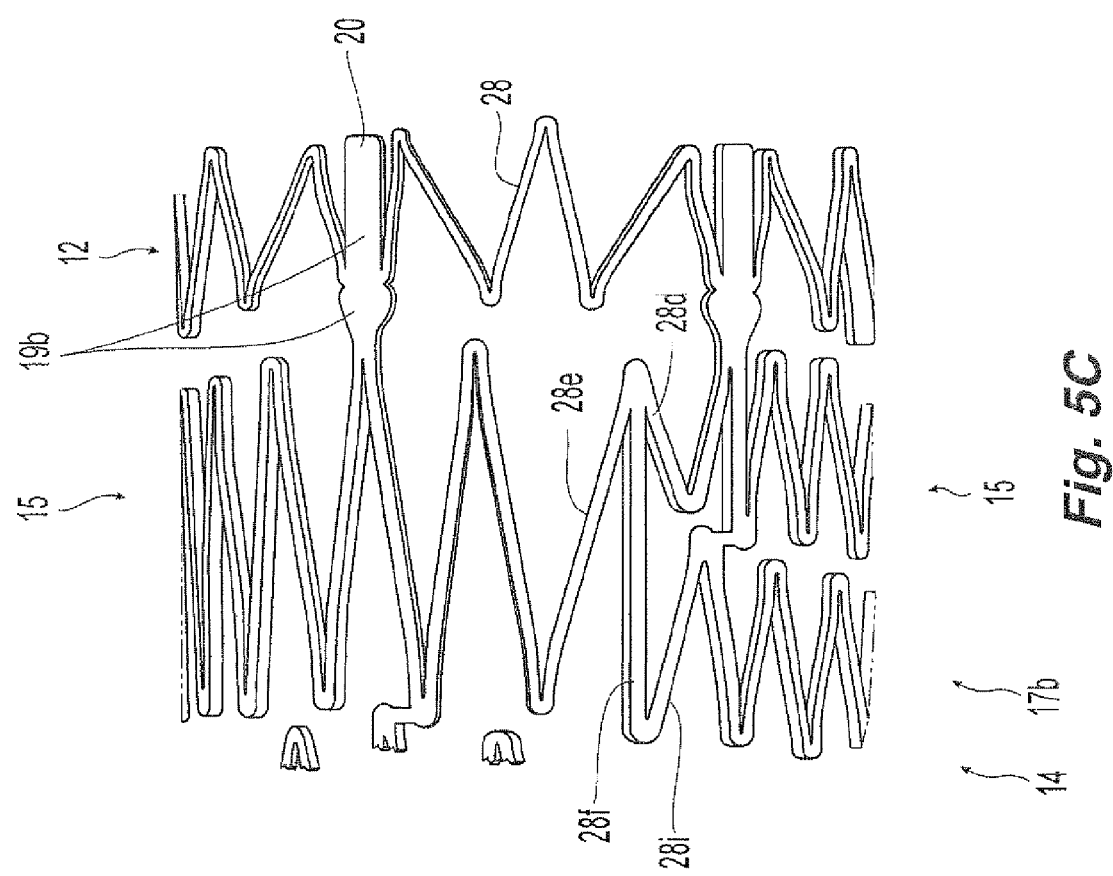
FIG. 5C illustrates a variation of the end portion of FIG. 5A.

In yet another alternative arrangement, illustrated in FIG. 5B, connecting strut 28f remains as in FIG. 5C while the first end strut 28d is deleted. In this embodiment, the connection strut 28f is connected to the connection strut 28g and the paddle 19b by bridge 18a.

As can be seen in FIGS. 5A-5C, the helical winding 16 of the coupling portion 15 is initially a short end strut 28 of the second end 7. The helical winding 16 (starting with the short strut) progressively increases in length in the direction of axis 8 as the winding 16 undulates (e.g., zig-zags about the longitudinal axis 8). As the winding 16 of coupling portion 15 progressively increases to fill in a gap between the second end portion 12 and the helical winding 16 of the intermediate portion 14, the winding 16 terminates while also coupling the second end portion 12 to the intermediate portion 14 without kinking or interference during loading or expansion. Multiple configurations provide for achievement of this result.

A first configuration is illustrated in FIG. 5A. In this configuration, a short segment, strut 28d, is directly connected to a long segment, strut 28e, while the initial helical winding 16 of the intermediate portion 14 is connected to a vertex 26 of two struts 28 via a bridge 18.

A second configuration is illustrated in FIG. 5B. In this configuration, a long strut, strut 28f, is directly connected to the first strut 28i of the intermediate portion 14. At the same time, a long strut 28f is connected to a short strut, strut 28g via bridge 18a.

A third configuration is illustrated in FIG. 5C. In this configuration, a long strut, strut 28f, is connected to both the first strut 28i of the intermediate portion 14 and a short strut, strut 28d, of the helical winding 16 of the coupling portion 15.

Figure 5D:
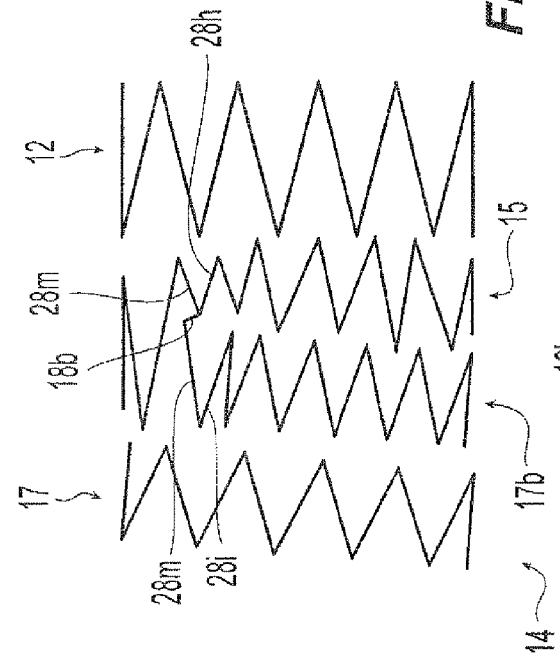
FIGS. 5D-5G are schematic views of the end portion of FIG. 5A illustrating variations of the interconnection between one helical winding having undulations of varying length to a helical winding having undulations of substantially constant length.
Figure 5F:
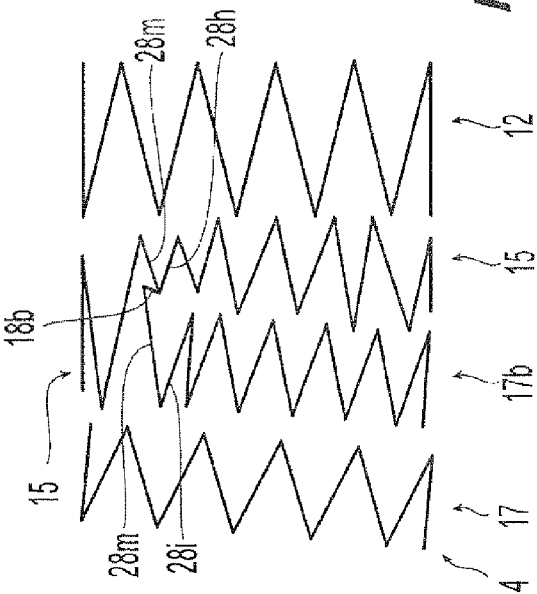
Figure 5E:
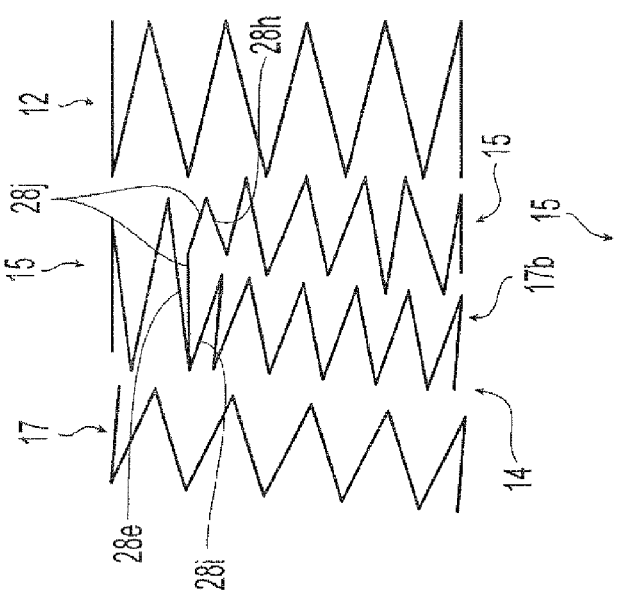

Other configurations to connect the helical winding 16 (of coupling portion 15) to the initial winding (circumferential section 17b of the intermediate portion 14) can be provided. For example, as shown in FIGS. 5D-5G, there are additional configurations available. In FIG. 5D, a short strut 28h and a long strut 28e of the winding 16 for coupling portion 15 are connected to the first strut 28i of the intermediate portion 14 via two unequal length struts 28j. In FIG. 5E, instead of two unequal length struts 28j, there are three unequal length struts

Figure 5G:
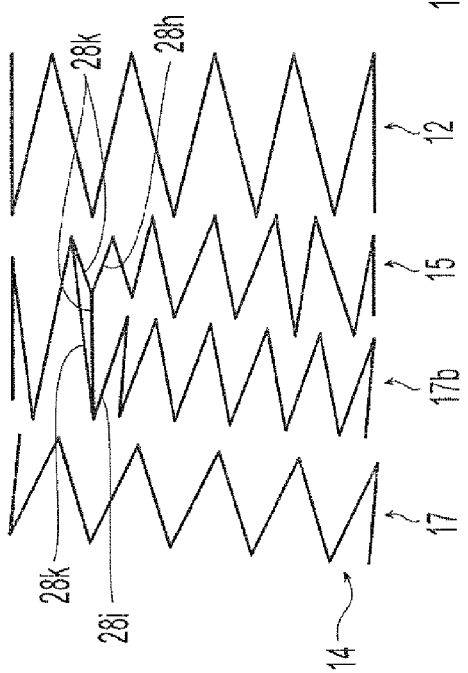

28*k*. In FIGS. 5F and 5G, two unequal length struts 28*m* can be connected with short bridges 18*b*.

The same configurations and alternatives illustrated and described with regard to the second end 7 can also be applied to the first end 5 of the stent to connect the helical winding 16 of the intermediate portion 14 (which has undulations of generally constant lengths along the longitudinal axis 8) to the winding of the first end portion 10 (which has undulations of varying lengths along the longitudinal axis 8).

Figure 7A:
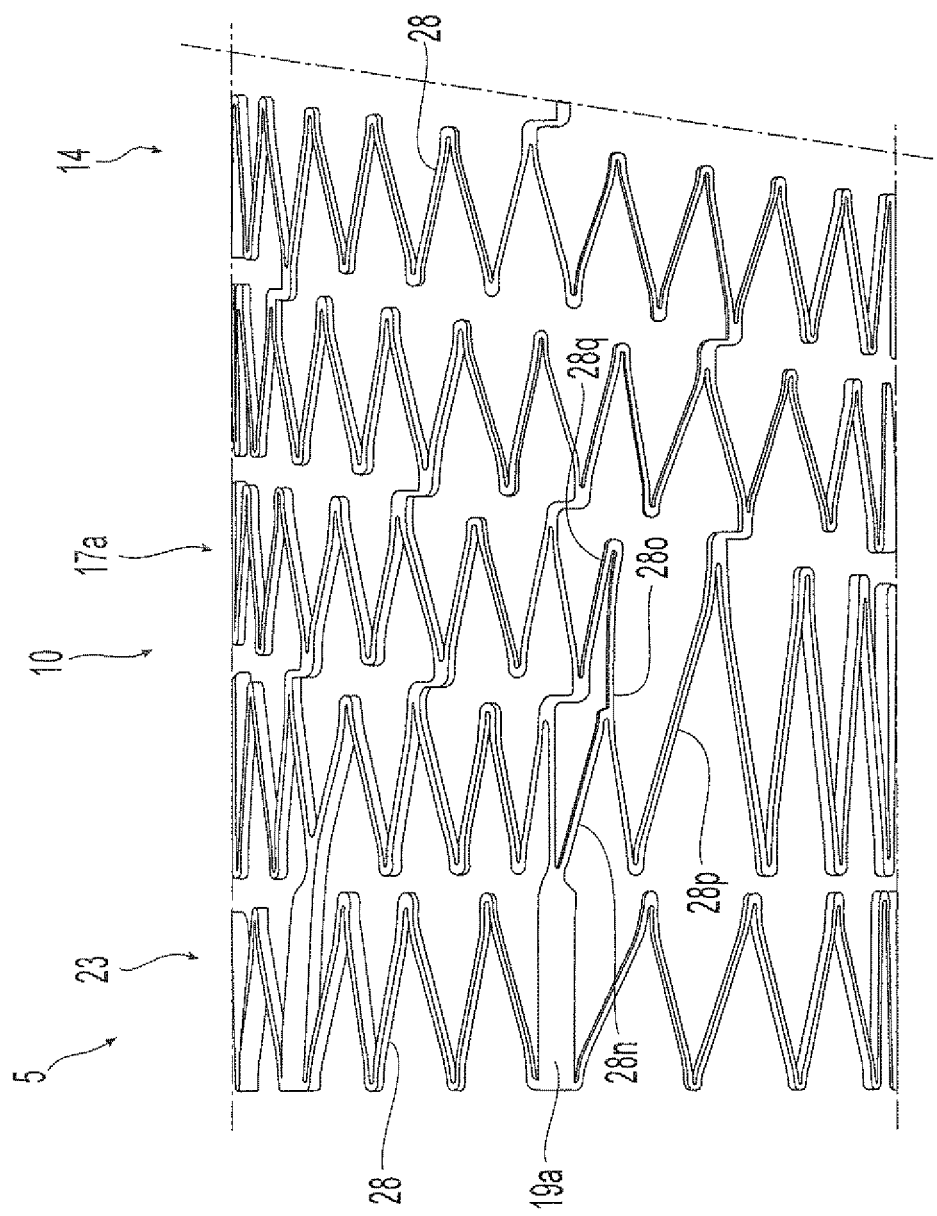
FIGS. 7A and 7B are close-up views of alternatives to FIG. 4.
Figure 7B:
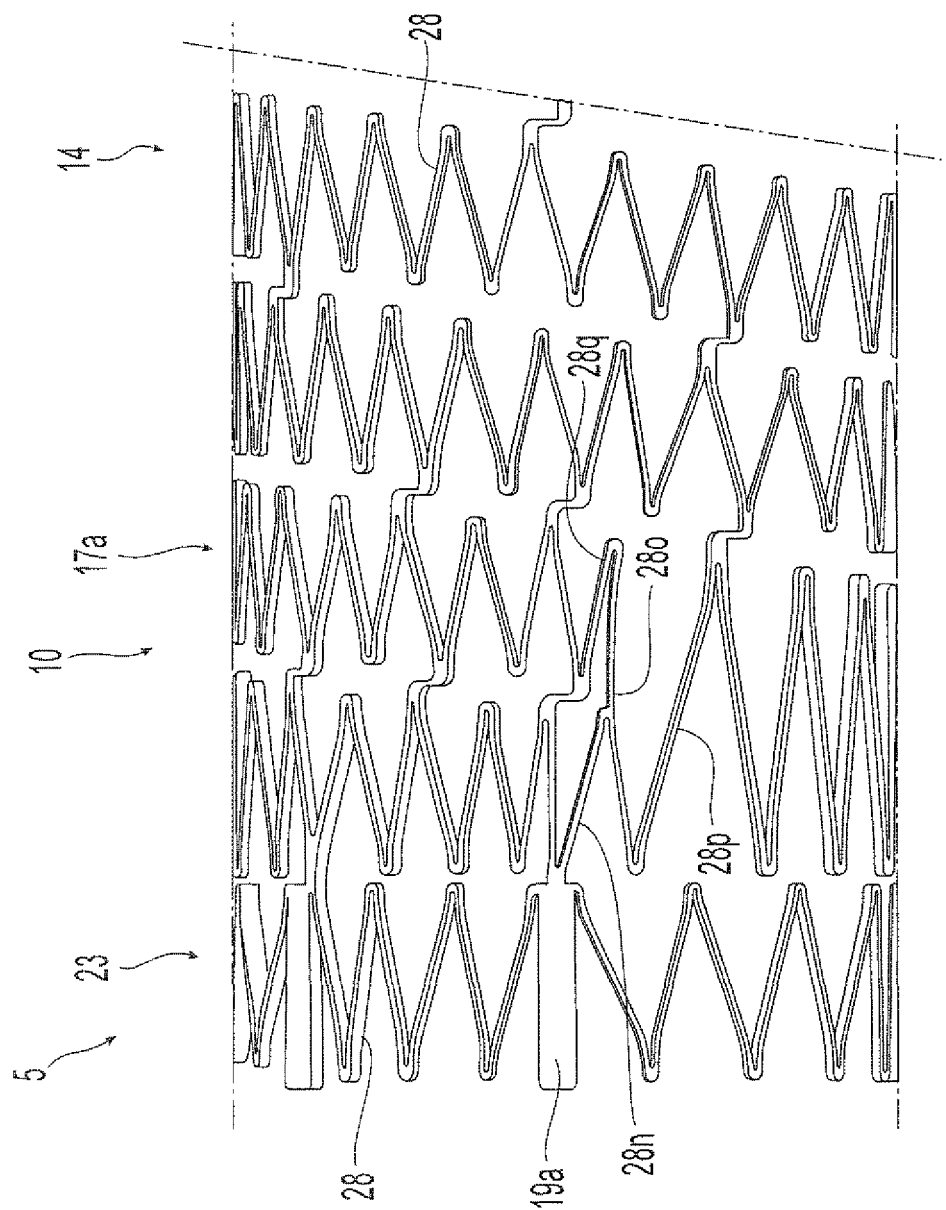

FIGS. 7A and B illustrate alternative arrangements of the first end 5 illustrated in FIG. 4. As illustrated, the first end 5 includes struts 28 between the paddles 19*a* to form an annular ring 23 similar to the annular ring 22 at the second end portion 12. As also illustrated, an initial strut 28*n* at the beginning of first end portion 10 is connected to a middle portion of a long strut 28*o*. Long strut 28*o* also connects to strut 28*p* of the first end portion 10 and to a first strut 28*q* of the intermediate portion 14 at the circumferential section 17*a*. Features identical to other embodiments are not identified again but can be altered with these end configurations. The same configurations and alternatives illustrated and described with regard to the first end 5 can also be applied to the second end 7 of the stent.

Regardless of the end (first end 5 or second end 7) utilized for the stent, the stent can be delivered using at least the following method. Initially, the stent 100 is compressed and loaded into a delivery sheath 200, illustrated in FIG. 6A. The sheath 200 Includes a flexible tubular end cone 202 that allows for the end 202*a* of the end cone 202 (FIG. 6A) to be distorted or enlarged towards a tubular form illustrated in FIG. 6B. To implant the stent 100, the delivery sheath 200 is transported over a guide wire 204 to the target site. Markers 20 mounted on the paddles 19 of the stent 100 or delivery sheath 200 allows for radiographic location of the delivery sheath 200 and stent 100. Once at the target site, the stent 100 is moved relative to the sheath 200 in the direction of arrow 201. In other words, the stent 100 can be pushed out by a boss portion 206 that engages the second end portion 12 of the stent 100 or the sheath 200 (not shown) can be pulled back so that the end cone 202 is flared over a tulip portion 208. Continued relative movement in the direction of the arrow 201 allows the stent 100 to be delivered outside of the sheath 200.

Bio-active agents can be added to the stent (e.g., either by a coating or via a carrier medium such as resorbable polymers) for delivery to the host vessel or duct. The bio-active agents can also be used to coat the entire stent. A coating can include one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters; vascular cell growth inhibitors such as growth factor inhibitors, growth factor receptor antagonists, transcriptional repressors, translational repressors, replication inhibitors, cell cycle inhibitors and activators inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; cytostatic or cytotoxic and agents which interfere with endogenous vascoactive mechanisms.

Genetic materials include anti-sense DNA and anti-sense RNA as well as other molecules working via the same mechanism of transcriptional or translational inhibition or activation. Genetic material also include (sense) DNA or (sense) RNA or equivalents thereof coding for Genes to replace defective or deficient endogenous molecules or Increase their amount or stability, or encode for non-endogenous or endogenous modified molecules with biological effects. Genetic material also includes nucleic acids affecting Gene expression or other cellular mechanisms by other ways than described above. Such Genetic materials could be organized "naked," packed with supporting molecules or in form of viruses or other vectors. Genes and their expression affected by above Genetic materials include but are not restricted to: tRNA or rRNA angiogenic factors including growth factors such as acidic and basic fibroblast growth factors, vascular endothelial growth factor, epidermal growth factor, transforming growth factor alpha and beta, platelet-derived endothelial growth factor, platelet-derived growth factor, tumor necrosis factor alpha, hepatocyte growth factor and insulin like growth factor, cell cycle inhibitors and activators including CD inhibitors, thymidine kinase ("TK") and other agents useful for interfering with cell proliferation, transcription factors, translation factors, the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-1, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them, Cells can be of human origin (autologous or allogeneic) or from an animal source (xenogeneic), genetically engineered if desired to deliver proteins of interest at the deployment site. The cells may be provided in a delivery media. The delivery media may be formulated as needed to maintain cell function and viability.

Suitable polymer materials as a coating or the base material may include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides including cellulose, chitin, dextran, polyesters including polyethylene terephthalate, polyacrylamides, polyethers, polyether sulfone, polycarbonate including tyrosine-derived polycarbonate, polyalkylenes including polypropylene, polyethylene and high molecular weight polyethylene and poly(butylene terephthalate) (PBT), halogenated polyalkylenes including polytetrafluoroethylene, polyurethanes, polyorthoesters, proteins (including fibrin und casein), polypeptides, silicones, siloxane polymers, polylactic acid (PLA), polyglycolic acid (PGA), poly(lactide-co-glycolide) (PLGA) polycaprolactone, polydioxanone, poly(g-ethyl glutamate), poly(DTH iminocarbonate), poly(bisphenol A iminocarbonate), poly(ortho ester), polycyanoacrylate, and polyphosphazene, polyhydroxybutyrate valerate and blends and copolymers thereof, coatings from polymer dispersions such as polyurethane dispersions (for example, BAYHDROL® fibrin, collagen and derivatives thereof, polysaccharides such as celluloses, starches, dextrans, alginates and derivatives, hyaluronic acid, squalene emulsions. Polyacrylic acid is particularly desirable.

The preferred stents may also be used as the framework for a vascular graft. Suitable coverings include nylon, collagen, PTFE and expanded PTFE, polyethylene terephthalate, KEVLAR® polyaramid, and ultra-high molecular weight polyethylene. More generally, any known graft material may be used including synthetic polymers such as polyethylene, polypropylene, polyurethane, polyglycolic acid, polyesters, polyamides, their mixtures, blends and copolymers.

Preferably, some or all of the bridges may be bio-resorbed while leaving the undulating strut configuration essentially unchanged. In other embodiments, however, the entire stent can be resorbed in stages by a suitable coating over the resorbable material. For example, the bridges can resorb within a short time period after implantation, such as, for example, 30 days. The remaining helical stent framework (made of a resorbable material such as metal or polymers) can thereafter resorb in a subsequent time period, such as, for example, 90 days to 2 years from implantation.

Markers 20 can be provided for all of the embodiments described above. The marker 20 can be formed from the same material as the stent 100 as long as the material is radiographic or radiopaque. The marker material can also be formed from gold, tantalum, platinum for example. One or more markers 20 can be formed from a marker material different from other markers.

The stents described herein can be, with appropriate modifications, delivered to an implantation site in a host with the delivery devices such as, for example, those shown and described in U.S. Patent Publication Nos. 2005/0090890 or 2002/0183826, and U.S. Pat. No. 6,939,352 or 6,866,669.

In addition to the tubular shape of the stent described in the illustrated embodiments, the framework of the stent can also be shaped to have different tubular sections with different outer diameters, to have a tubular section coupled to a conic section, or to have a single cone. The struts of the stent can be wire-like members, and have cross-sections that are circular, rectangular, square, or polygonal.

Even though various aspects of the preferred embodiments have been described as self-expanding, Nitinol stents suitable for use in the common bile duct or superficial femoral artery, it should be apparent to a person skilled in the art that features of the illustrated embodiments can be applied to self-expanding stents of all sizes and made from any suitable material. Further, such stents can be applied to any body lumen where It is desired to place a structure to maintain patency, prevent occlusive disease, or for other medical purposes, such as to hold embolization devices in place. Further, the features described in the embodiments can be applied to balloon-expanded stents made from malleable or formable materials and intended to be expanded inside a suitable body lumen. The features described in the embodiments can also be applied to bare metal stents, stents made from other than metallic materials, stents with or without coatings intended for such purposes as dispensing a medicament or preventing disease processes, and stents where some or all of the components (e.g., struts, bridges, paddles) of the stents are biodegradable or bio-resorbable.

The embodiments use the example of a 6 mm self-expanding stent, but can be applied with equal merit to other kinds of stents and stents of other sizes. Specifically, stents for use in peripheral arteries are customarily made in outer diameters ranging from 3 mm to 12 mm, and in lengths from 10 mm to 200 mm. Stents of larger and smaller diameters and lengths can also be made accordingly. Also, stents embodying the features of the embodiments can be used in other arteries, veins, the biliary system, esophagus, trachea, and other body lumens.

Self-expansible stent matrices must satisfy rigorous failure testing procedures which prompts designers to optimize stress levels throughout the matrix of struts of the stent. The struts are beams that undergo bending stresses. Thus, stress optimization results in struts exhibiting modulated transverse cross-sectional areas along the length of each strut, but struts will generally all look much the same, in terms of shape, width and thickness (at least when they are all much the same length).

Occasional oversized struts or "paddles" would be seen as a negative design feature in that, for no good reason, they prevent the strut designer from maximizing the ratio of diameters in the radially compressed and expanded configurations of the stent. For any particular starting tube of stent material, the more paddles in the circumference, the less will be the ultimate working diameter to which the stent can be radially expanded.

However, the penalty of a smaller ultimate diameter might be tolerable if the paddles provide such a useful positive function that the loss of diameter is a worthwhile sacrifice. One such positive function is to provide a radiopaque marker function. Another is to provide an attachment edge, within the thickness of the stent matrix annulus, for a marker of more radiopaque material than the material of the stent matrix, as such.

Thus, from the paddle concept we can progress to an additional contribution to the art, namely a self-expansible stent with radiopaque markers that can be described as follows. This further invention relates to a radially self-expansible stent with a plurality of radiopaque markers attached to at least one of its ends.

Vascular stents are commonly used for the treatment of various vessel diseases. They are implanted transluminally using a catheter delivery system, to advance them to a stenting site, where they expand in order to widen the clogged or narrowed blood vessel. During the implantation procedure, the exact position of the stent within the vessel is monitored, mainly using X-ray imaging techniques. In order to ensure accurate placement, a good visibility of the stent is crucial. In general, this is achieved by attaching suitable markers which are made from materials with a radiopacity larger than that of the stent material. In addition, these markers have to be sufficiently large to provide a good X-ray contrast. For a precise determination of the stent position during delivery, it is advantageous to place the markers at both ends of the stent.

A tubular stent with a plurality of radiopaque markers attached to selected inflection zones around its circumference is disclosed in WO-A-2002/015820. The markers are spoon-shaped in a way that almost a complete ring of marker material is formed in the radially compressed state of the stent, providing a particularly high level of radiopacity during transluminal delivery. Thereby, an increase in visibility to radiation is achieved without any increase in the wall thickness of the stent at the position of the markers, maintaining a large radial opening for fluid flow as well as a small cross-sectional profile. Ideally, the number of markers in such a ring of markers as described above is to be kept small, so that each marker is large enough to facilitate sufficient visibility even in the radially expanded state of the stent. Furthermore, the number of marker/inflection zone joints should be kept at a minimum in order to reduce the risk of loss of a marker in the body following failure of such a joint after the stent has been placed.

For the case of self-expansible stents, delivery to the narrowed portion of the blood vessel is performed with the use of a co-axial catheter delivery system. Hereby, the stent is kept in its radially compressed state by an outer sheath. A co-axial cylinder inside the sheath is used for displacing the stent axially, relative to the outer sheath. Once the stent has been placed at the desired position within the vessel, the outer sheath is withdrawn while the inner cylinder pushes against one end of the compressed stent, precipitating the release of the stent from the delivery system. This procedure can impose on a stent such as the one disclosed in WO-A-2002/015820 stresses concentrated on the radiopaque markers which protrude axially beyond the axial end of the matrix of struts of the stent annulus. This stress, concentrating at the joints between the markers and the inflection zones from which they are cantilevered has been identified as a feature that can and should be reduced or even eliminated.

The main objective of the present further invention is to provide a self-expansible stent with radiopaque markers attached to it that offers a high degree of mechanical stability during release of the stent from the delivery system while maintaining a good visibility upon exposure to radiation. This aim is achieved by a self-expansible stent with the technical features of claim 96. Preferred embodiments of the further invention follow from subclaims 97-112.

The present further invention provides a radially self-expansible stent with two end annuli for delivery by a co-axial catheter delivery system. The end annulus to be pushed during release of the stent has a plurality of spaced inflection zones distributed in its circumference, some of which carry a radiopaque marker. The idea is to get all the inflection zones to share the release stresses, not just the ones that carry a radiopaque marker. In general, the term "inflection zone" as used herein refers to a region where two or more strut ends are connected or where two or more struts intersect. It is, however, not restricted to this interpretation. A large number of different strut patterns are being used, or have at least been proposed, for tubular stents. Each of these patterns will have points which define an end to the stent tube and which allow for the attachment of a marker. Our definition of the term "inflection zone" is such that these end points are included.

The radiopaque markers are shaped and located on the selected inflection zones such that the compressive stress exerted on the end annulus during release of the stent is shared between the markers and the inflection zones that do not carry a marker. In this way, the strain on the marker/inflection zone joints is minimised, reducing the risk of physical damage, such as breakage or deformation. This concept is applicable to any stent design and allows for the use of only a small number of markers while the stability of the stent is secured. Keeping the number of markers at a minimum has significant advantages. First, having fewer marker/inflection zone joints reduces the danger of severed or bent markers. Self-expansible stents are extremely elastic but nevertheless not invulnerable to distortion. Fatigue performance is of vital importance with vascular stents, which flex with every heartbeat. Any stress that a stent matrix suffers locally, that exceeds the maximum planned for in the Government regulatory fatigue-testing protocol can adversely affect the fatigue life of the stent. This fact emphasizes the importance of a robust stent design, since even the slightest damage to the joints occurring during the release of the stent may shorten the service life of the stent. Furthermore, the circumference of the ring formed by the ensemble of markers in the radially compressed state of the stent is limited by the circumference of the stent tube itself. Thus, keeping the number of markers small allows for larger marker sizes and consequently an improved visibility of the stent in the radially expanded state.

So-called "ring stents" exhibit a plurality of rings arranged along their axial length which are interconnected between ring ends and have a plurality of inflection zones distributed in the circumference of the ring ends. In one embodiment, each of these ring ends comprises more inflection zones than the end annulus of the stent. Since, In the radially compressed state, the stent has a homogeneous circumference throughout its structure, the circumference of the end annulus of the stent will be the same as that of the ring ends, despite comprising less inflection zones. Therefore, the circumferential extent of the inflection zones that carry a marker can be increased, allowing for the attachment of larger markers, which is advantageous for reasons of visibility as discussed above. Even more space for the markers can be created within the end annulus of the stent if the inflection zones of the end annulus of the stent that do not carry a marker have a smaller circumferential extent than the inflection zones distributed in the circumference of the ring ends. Therefore, the above arrangement facilitates a possible increase in marker size without changing the number of inflection zones of the stent rings which may affect the mechanical properties of the stent, such as stability and elasticity.

A further way of creating more space for the markers within the end annulus of the stent is given in another preferred embodiment, where the inflection zones of the end annulus of the stent that do not carry a marker have a larger axial length parallel to the long axis of the stent than the inflection zones distributed in the circumference of the ring ends.

Preferably, the markers are bonded to the inflection zones at a glue interface, more preferably, by a weld. The form of the weld is hereby determined by the shape and the size of the marker.

In a preferred embodiment, the inflection zones that carry a marker differ in shape, size or both shape and size from the inflection zones that do not carry a marker. The inflection zones that carry a marker may, for example, have a smaller size so as to leave more space for the attached markers or a shape particularly suited for a certain type of weld (depending on the shape and size of the marker). In one embodiment, each inflection zone is present as a stem with an axial length parallel to the long axis of the stent. Preferably, the inflection zone stems that carry a marker have a smaller length than the inflection zone stems that do not carry a marker. This arrangement allows for the accommodation of portions of the markers (or even whole markers) between the neighbouring longer inflection zones.

Preferably, the markers and the inflection zones have the same thickness but markers with a greater radial thickness are not excluded. On the one hand, an increase in marker thickness beyond the stent annulus wall thickness is not desirable, since a large radial opening for fluid flow as well as a small cross-sectional profile of the stent ought to be maintained. On the other hand, both the radiopacity and the mechanical properties of the markers depend on their thickness. Consequently, too thin a marker will give a poor contrast when exposed to radiation and may be prone to deformation or even breakage.

In a preferred embodiment, each marker subtends a larger arc of the circumference of the end annulus than each inflection zone that does not carry a marker, improving the visibility of the stent ends.

A number of different materials may be used for the fabrication of the stent and the radiopaque markers of this further invention. Preferably, the stent is made from a nickel titanium shape memory alloy. Such an alloy provides the mechanical properties necessary for reliable stent operation, namely a high degree of elasticity and physical stability. The radiopaque markers are preferably made from tantalum, gold, or a ternary alloy made from nickel, titanium and a third, radiopaque metal. All these metals offer a high level of radiopacity. Both the above stent and marker materials are non-toxic and provide a good biological compatibility with the human body. For nickel titanium stents, markers of tantalum are of special interest because their electrochemical potentials are so similar.

In another preferred embodiment, the markers do not extend axially beyond the inflection zones which do not carry a marker, in the radially compressed state of the stent. This arrangement can be accomplished, for example, by making the inflection zones that carry a marker shorter than the ones that do not carry a marker. Preferably, during release of the stent from the delivery system, the markers and the inflection zones which do not carry a marker are both in physical contact with the pushing part of the delivery system, i.e., the co-axial inner cylinder. In such a configuration, the compressive stress exerted on the end annulus during release of the stent is shared between the markers and the inflection zones without markers, minimising the risk of physical damage to the stent. A marker size large enough for excellent visibility can still be maintained by choosing a small number of inflection zones in the end annulus of the stent and by making the inflection zones that carry a marker sufficiently short.

In another preferred embodiment, portions of the periphery of the markers rest on the neighbouring inflection zones in the radially compressed state of the stent, such that the compressive stress exerted by the delivery system on the markers during release of the stent is delivered to the neighbouring inflection zones by the markers. Preferably, in this configuration the markers stand axially proud of the inflection zones that do not carry a marker. In this configuration, an increase in marker size can be achieved, while the distribution of the applied pressure between markers and inflection zones without markers is still maintained.

DETAILED DESCRIPTION OF FURTHER PREFERRED EMBODIMENTS

Figure 8:
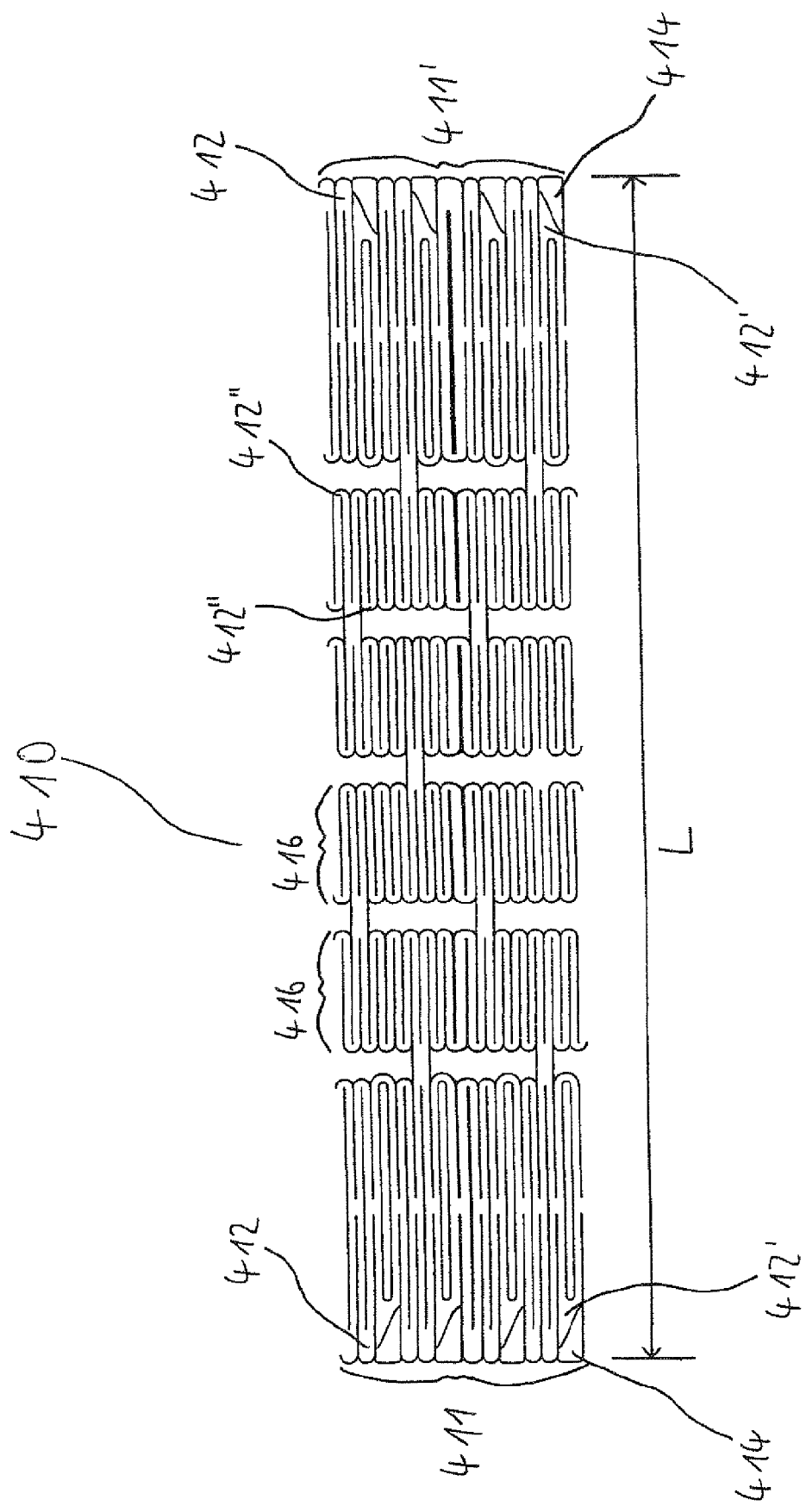
FIG. 8 shows a laser cutting of a stent with radiopaque markers attached to it, according to a first further preferred embodiment.

FIG. 8 shows a laser cutting of a radially self-expansible stent 410 made from Nitinol with radiopaque markers 414 made from Tantalum attached, according to a first further preferred embodiment. The markers 414 are welded to the inflection zones 412' and extend as far as the inflection zones that do not carry a marker 412. In this way, the compressive stress exerted on the end annulus 411 during release of the stent is shared between the markers 414 and the inflection zones that do not carry a marker 412. The stent comprises four interconnected rings 416 with fourteen inflection zones 412" in the circumference of each ring end. In contrast to this, the end annuli 411, 411' only have twelve inflection zones 412, 412'. This allows for a larger circumferential extent of the inflection zones 412' and the markers 414 attached thereto since the circumferential extent of the inflection zones 412 is identical to that of the inflection zones 412". In addition to this, the axial length of inflection zones 412 is larger than that of inflection zones 412", allowing for longer markers. Thus, the present embodiment is specifically designed for accommodating large markers 414 in order to optimise the visibility of the stent 410.

FIG. 9 shows one end of a laser cutting of a stent 410 made from Nitinol with radiopaque markers 414 made from Tantalum attached to it, according to a second further preferred embodiment. The markers 414 are welded to the inflection zones 412' and stand axially proud of the inflection zones 412 that do not carry a marker 414. As can be seen, the shape of inflection zones 412' is adapted in order to allow for a robust welded connection with marker 414 and differs significantly from that of inflection zones 412. The increased circumferential extent of inflection zones 412' as compared to inflection zones 412 is facilitated by the difference in the number of inflection zones 412, 412', 412" between the ends of rings 416 and the end annulus 411, analogous to the first preferred embodiment. Furthermore, inflection zones 412 have grooves 418 at their top ends which are shaped to accommodate the peripheral portions of the T-shaped markers 414 in the radially compressed state of the stent 410. In this way, despite the fact that during the release of the stent 410 only the markers 414 are in physical contact with the pushing part of the delivery system, the compressive stress exerted on the markers is shared between the markers and the neighbouring inflection zones. The present configuration allows for the accommodation of particularly large markers 414 while at the same time maintaining the stability of the stent 410. FIG. 10 shows a portion of the end annulus 411 in the radially expanded state of the stent 410, according to the present embodiment. Here, the grooves 418 are more clearly visible.

While the invention has been described In terms of particular variations and illustrative figures, those of ordinary skill in the art will recognize that the invention is not limited to the variations or figures described. In addition, where methods and steps described above indicate certain events occurring in certain order, those of ordinary skill In the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. An implant, comprising:
   a tubular intermediate portion defining a first helical winding and a longitudinal axis;
   a tubular end portion defining a different second helical winding and disposed adjacent to an end of the intermediate portion: and
   a paddle disposed adjacent to the end portion,
   the intermediate and end portions including a plurality of struts and bridges, each strut having an end connected to an end of an adjacent strut, each bridge connected to an end of a strut, the intermediate and end portions each having an end strut disposed proximate to an end of each helical winding, and the paddle having a length and opposing ends disposed parallel to the longitudinal axis, an end of the paddle directly connected to a paddle strut directly connected to a paddle bridge, one of the end struts directly connected to the paddle bridge.

2. The implant of claim 1, the paddle having a circumferential width that is greater than a circumferential width of the paddle strut.

3. The implant of claim 1, the implant further comprising a ring portion disposed adjacent to the end portion.

4. The implant of claim 3, the implant further comprising another tubular end portion disposed at an opposing end of the intermediate portion.

5. The implant of claim 4, the another tubular end defining a third helical winding different from the first and second helical windings.

6. The implant of claim 4, the implant further comprising another ring portion disposed adjacent to the another tubular end portion.

7. The implant of claim 1, wherein the end stmt of the end portion includes a generally linear portion that connects the end portion to the intermediate portion.

8. The implant of claim 1, wherein the first helical winding of the intermediate portion defines a plurality of circumferential sections disposed along the longitudinal axis, the intermediate portion including at least one bridge configured to connect one circumferential section to an adjacent axially-spaced circumferential section, the at least one bridge extending on a plane generally orthogonal with respect to the longitudinal axis.

9. The implant of claim 8, wherein the first helical winding of the intermediate portion includes a bridge strut directly connected to the at least one bridge, the bridge strut having a length greater than a length of at least one of the plurality of struts of the intermediate portion.

10. The implant of claim 1, wherein at least one paddle is a rectangular marker having a length extending generally parallel to the longitudinal axis and a width greater than two times the circumferential width of at least one of the plurality of struts.

11. The implant of claim 1, wherein a first number of struts between any two bridges in a first circumferential direction along the first helical winding of the intermediate portion is equal to a second number of struts between any two bridges in a second circumferential direction opposite to the first circumferential direction.

12. The implant of claim 1, wherein a first number of struts disposed between any two bridges in a first circumferential direction along the first helical winding of the intermediate portion is not equal to a second number of struts disposed between any two bridges in a second circumferential direction opposite to the first circumferential direction.

13. The implant of claim 1, wherein the paddle includes a marker comprising a radiopaque material disposed in a recess of the paddle.

14. An implant, comprising:
an intermediate portion having a first continuous helical winding defining a plurality of circumferential sections circumscribing a longitudinal axis from a first end to a second end to define a portion of essentially a tube, the circumferential sections being spaced apart along the longitudinal axis, each circumferential section having undulations disposed about a portion of the tube;
a first end portion disposed proximate the first end, the first portion having a second continuous helical winding that circumscribes a portion of the longitudinal axis, the second continuous helical winding having undulations of increasing lengths;
a second end portion disposed proximate the second end, the second portion having undulations that circumscribe the longitudinal axis to define a ring;
a coupling portion that connects the second portion to the intermediate portion, the coupling portion having a third continuous helical winding that circumscribes a portion of the longitudinal axis; and
a paddle disposed adjacent to the first portion, the paddle having a length and opposing ends disposed parallel to the longitudinal axis, an end of the paddle directly connected to a paddle strut directly connected to a paddle bridge, at least one end strut of the intermediate portion directly connected to the paddle bridge.

15. The implant of claim 14, an end strut of the first end portion directly connected to the paddle bridge.

16. The implant of claim 15, at least one of a plurality of struts directly connected to the paddle bridge.

17. The implant of claim 14, an end strut of the coupling portion directly connected to the paddle bridge.

18. The implant of claim 14, the paddle having a circumferential width that is greater than a circumferential width of any one of a plurality of struts comprising the first, second, and third helical windings.

* * * * *